(12) United States Patent
Bowser

(10) Patent No.: US 7,572,596 B2
(45) Date of Patent: Aug. 11, 2009

(54) MODULATION OF THE NEUROENDOCTRINE SYSTEM AS A THERAPY FOR MOTOR NEURON DISEASE

(75) Inventor: Robert P. Bowser, Cranberry Township, PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 132 days.

(21) Appl. No.: 11/294,161

(22) Filed: Dec. 2, 2005

(65) Prior Publication Data

US 2006/0178306 A1    Aug. 10, 2006

Related U.S. Application Data

(60) Provisional application No. 60/632,450, filed on Dec. 2, 2004.

(51) Int. Cl.
*G01N 33/53* (2006.01)
*G01N 33/535* (2006.01)
*G01N 33/72* (2006.01)

(52) U.S. Cl. .................. 435/7.1; 435/7.9; 435/7.91; 435/7.92; 436/173; 436/174; 436/501

(58) Field of Classification Search ............... None
See application file for complete search history.

(56) References Cited

U.S. PATENT DOCUMENTS 6,618,138 B2   9/2003   Khoury
6,776,984 B1   8/2004   Schwartz

FOREIGN PATENT DOCUMENTS

WO    WO 93/24834 A1    12/1993
WO    WO 98/59360 A1    12/1998

OTHER PUBLICATIONS

Ranganathan et al., J Neurochem. 2005; 29: 1461-1471.*
Yokota et al., Acta Neuropathol. 2006; 112: 633-645.*
Aizawa et al., J. Neuro Sci. 2000; 175: 109-113.*
Wada et al. Acta Neuropathol. 1999; 98: 150-156.*
Berg et al. Exploring Proteins, in Biochemistry, fifth edition, 2002 by W. H. Freeman and Company, New York, New York, 10010; relevant chapter portions downloaded on Jan. 14, 2007 at ncbi.nlm.nih.gov/books/bv.fcgi?highlight=immunological%20techniques&rid=stryer.section.506#507; 10 pages total downloaded.*
Ono et al. Acta Neurol Scand. 2000; 102: 47-52.*
Cudkowicz et al., "Measures and Markers in Amyotrophic Lateral Sclerosis," *NeuroRX: The Journal of the American Society for Experimental NeuroTherapeutics*, 1(2): 273-283 (Apr. 2004).
Abrahamson, et al., "The human cystatin C gene (CST3), mutated in hereditary cystatin C amyloid angiopathy, is located on chromosome 20", *Hum. Genet.*, 82(3):223-6 (1989).
Asgeirsson, et al., "Hereditary cystatin C amyloid angiopathy: monitoring the presence of the Leu-68 —> Gln cystatin C variant in cerebrospinal fluids and monocyte cultures by MS", *Biochem. J.*, 329 (Pt 3):497-503 (1998).
Carrette, et al., "A panel of cerebrospinal fluid potential biomarkers for the diagnosis of Alzheimer's disease", *Proteomics*, 3(8):1486-94 (2003).
Deng, et al., "Elevation of cystatin C in susceptible neurons in Alzheimer's disease", *Am. J. Pathol.*, 159(3):1061-8 (2001).
Kato, et al., "A neurosphere-derived factor, cystatin C, supports differentiation of ES cells into neural stem cells", *Proc. Natl. Acad. Sci. U.S.A.*, 103(15):6019-24 (2006).
Lofberg, et al., "Immunohistochemical characterization of the amyloid deposits and quantitation of pertinent cerebrospinal fluid proteins in hereditary cerebral hemorrhage with amyloidosis", *Stroke*, 18(2):431-40 (1987).
Nagai, et al., "Cystatin C and cathepsin B in CSF from patients with inflammatory neurologic diseases", *Neurology*, 55(12):1828-32 (2000).
Okamoto, et al., "Bunina bodies in amyotrophic lateral sclerosis immunostained with rabbit anti-cystatin C serum", *Neurosci. Lett.*, 162(1-2):125-8 (1993).
Sanchez, et al., "Cystatin C as a potential cerebrospinal fluid marker for the diagnosis of Creutzfeldt-Jakob disease", *Proteomics*, 4(8):2229-33 (2004).
XU, et al., "Cystatin C prevents degeneration of rat nigral dopaminergic neurons: in vitro and in vivo studies", *Neurobiol. Dis.*, 18(1):152-65 (2005).
U.S. Appl. No. 11/294,326, filed Dec. 2, 2005, Bowser.
U.S. Appl. No. 60/513,930, filed Oct. 23, 2003, Bowser et al.
U.S. Appl. No. 60/632,380, filed Dec. 2, 2004, Bowser.
Arrahamson et al., "Structure and Expression of the Human Cystatin C Gene," *The Biochemical Journal*, 268(2): 287-294 (Jun. 1, 1990).
Benson et al., "Identification of Carriers of a Variant Plasma Prealbumin (Transthyretin) Associated With Familial Amyloidotic Polyneuropathy Type I," *The Journal of Clinical Investigation*, 75: 71-75 (1985).
Bergen et al., "Identification of Transthyretin Variants by Sequential Proteomic and Genomic Analysis," *Clinical Chemistry*, 50(9): 1544-1552 (2004).
Bernstein et al., "Transthyretin: Its Response to Malnutrition and Stress Injury" *Clin Chem Lab Med*, 40(12): 1344-1348 (2002).

(Continued)

*Primary Examiner*—Bridget E Bunner
*Assistant Examiner*—Christina Borgeest
(74) *Attorney, Agent, or Firm*—Pabst Patent Group LLP

(57) ABSTRACT

The invention provides a method for treating amyotrophic lateral sclerosis (ALS) in a subject. The method comprises administering to the nervous system of the subject a composition comprising a thyroxine protein or a therapeutic fragment or pharmacologic mimic thereof and a pharmaceutically acceptable carrier. The invention also provides a method for treating ALS in a subject that comprises administering to the subject a transthyretin protein, 7B2 protein, a cystatin C protein, a neuroendocrine protein, a cysteine protease inhibitor, or an inhibitor of an enzyme that processes a 7B2 protein. In addition, the invention provides methods for determining the susceptibility of a subject to developing ALS and for determining the progression of ALS in a subject.

11 Claims, 8 Drawing Sheets

OTHER PUBLICATIONS

Borchelt et al., "Superoxide Dismutase 1 With Mutations Linked to Familial Amyotrophic Lateral Sclerosis Possesses Significant Activity," *Proc. Natl. Acad. Sci. USA*, 91(17): 8292-8296 (Aug. 16, 1994).

Bowser et al., "Protein Profiling of Amyotrophic Lateral Sclerosis Patients by Mass Spectrometry," *the FASEB Journal*, 17(4). A658 (2003).

Chaudhuri et al., "The Neuroendocrine Protein 7B2 Acts as a Molecular Chaperone in the In Vitro Folding of Human Insulin-Like Growth Factor-1 Secreted From Yeast," *Biochemical and Biophysical Research Communications*, 211(2): 417-425 (Jun. 15, 1995).

Cleveland et al., "From Charcot to Lou Gehrig: Deciphering Selective Motor Neuron Death in ALS," *Nature Review Neuroscience*, 2: 806-819 (Nov. 2001).

Connors et al., "Tabulation of Human Transthyretin (TTR) Variants, 2003," *Amyloid*, 10(3): 160-184 (Sep. 2003).

Corcoran et al., "Absence of Retinoids Can Induce Motoneuron Disease in the Adult Rat and a Retinoid Defect is Present in Motoneuron Disease Patients," *Journal of Cell Science*, 115(24): 4735-4741 (Dec. 15, 2002).

Desnuelle et al., "A Double-Blind, Placebo-Controlled Randomized Clinical Trial of α- Tocopherol (Vitamin E) in the Treatment of Amyotrophic Lateral Sclerosis," *ALS and Other Motor Neuron Disorders*, 2(1): 9-18 (2001).

Feigenbaum et al., "Dentral and Meta-Dendral: Roots of Knowledge Systems and Expert System Applications," *Artificial Intelligence*, 59: 233-240 (1993).

Fernandez et al., "Thyroid Hormone Administration Enhances Remyelination in Chronic Demyelinating Inflammatory Disease," *Proc. Natl. Acad. Sci. USA*, 101(46): 16363-16368 (Nov. 16, 2004).

Goodall et al., "Association of the H63D Polymorphism in the Hemochromatosis Gene with Sporadic ALS," *Neurology*, 65(6): 934-937.

Groeneveld et al., "A Randomized Sequential Trail of Creatine in Amyotrophic Lateral Sclerosis," *Annals of Neurology*, 53(4): 437-445 (Apr. 2003).

Gurney et al., "Motor Neuron Degeneration in Mice that Express a Human Cu, Zn Superoxide Dismutase Mutation," *Science*, 264: 1772-1775 (Jun. 17, 1994).

Gurney et al., "Benefit of Vitamin E, Riluzole, and Gabapentin in a Transgenic Model of Familial Amyotrophic Lateral Sclerosis," *Annals of Neurology*, 39(2): 147-157 (Feb. 1996).

Hillenkamp et al., "Matrix Assisted UV-Laser Desorption/Ionization: A New Approach to Mass Spectrometry of Large Biomolecules," *Biological Mass Spectrometry*, (Burlingame and McCloskey, eds) Elsevier, Amsterdam, 49-60 (1990).

Jellinger, "Neuropathological Spectrum of Synucleinopathies," *Movement Disorders*, 18(Supplement6): S2-S12 (2003).

Kamel et al., "Lead Exposure and Amyotrophic Lateral Sclerosis," *Epidemiology*, 13(3): 311-319 (May 2002).

Kim et al., "PARP Expression is Increased in Astrocytes but Decreased in Motor Neurons in the Spinal Cord of Sporadic ALS Patients," *Journal of Neuropathology and Experimental Neurology*, 62(1): 88-103 (Jan. 2003).

Kriz et al., "Efficient Three-Drug Cocktail for Disease Induced by Mutant Superoxide Dismutase," *Annals of Neurology*, 53(4): 429-436 (Apr. 2003).

Lee et al., "Carcinogenicity Predictions for a Group of 30 Chemicals Undergoing Rodent Cancer Bioassays Based on Rules Derived from Subchronic Organ Toxicities," *Environmental Health Perspectives*, 104(Supplement5): 1059-1063 (Oct. 1996).

Levy et al., "Stroke in Icelandic Patients with Hereditary Amyloid Angiopathy is Related to a Mutation in the Cystatin C Gene, An Inhibitor of Cysteine Proteases," *The Journal of Experimental Medicine*, 169(5): 1771-1778 (May 1, 1989).

Lin et al., "Large-scale protein identification using mass spectrometry," *Biochimica et Biophysica Acta*, 1646(1-2): 1-10 (2003).

Martens, "Cloning and Sequence Analysis of Human Pituitary cDNA Encoding the Novel Polypeptide 7B2," *FEBS Letters*, 234(1): 160-164 (1988).

Martens et al. "The Novel Pituitary Polypeptide 7B2 is a Highly-Conserved Protein Coexpressed with Proopiomelanocortin," *European Journal of Biochemistry*, 181(1): 75-79 (Apr. 1989).

Mbikay et al., "Neuroendocrine Secretory Protein 7B2: Structure, Expression and Functions," *Biochemical Journal*, 357(2): 329-342 (Jul. 15, 2001).

Menzies et al., "Mitochondrial Dysfunction in a Cell Culture Model of Familial Amyotrophic Lateral Sclerosis," *Brain*, 125(7): 1522-1533 (Jul. 2002).

Mey et al., "Retinoic Acid Signaling in the Nervous System of Adult Vertebrates," *The Neuroscientist*, 10(5): 409-421 (2004).

Miller et al., "Riluzole for Amyotrophic Lateral Sclerosis (ALS)/ Motor Neuron Disease (MND)," *ALS and Other Motor Neuron Disorders*, 4(3): 191-206 (Sep. 2003).

Mita et al., "Cloning and Sequence Analysis of cDNA for Human Prealbumin," *Biochemical and Biophysical Research Communications*, 124(2): 558-564 (Oct. 30, 1984).

Nagai et al., "Rats Expressing Human Cytosolic Copper-Zinc Superoxide Dismutase Transgenes with Amyotrophic Lateral Sclerosis: Associated Mutations Develop Motor Neuron Disease," *The Journal Of Neuroscience*, 21(23): 9246-9254 (Dec. 1, 2001).

Ong et al., "An Evaluation of the Use of Two-Dimensional Gel Electrophoresis in Proteomics," *Biomolecular Engineering*, 18(5): 195-205 (Nov. 2001).

Palha, "Transthyretin as a Thyroid Hormone Carrier: Function Revisited," *Clinical Chemistry and Laboratory Medicine*, 40(12): 1292-1300 (Dec. 2002).

Paquet et al., "The Neuroendocrine Precursor 7B2 is a Sulfated Protein Proteolytically Processed by a Ubiquitous Furin-Like Convertase," *The Journal of Biological Chemistry*, 269(30): 19279-19285 (Jul. 29, 1994).

Paulson, "Protein Fate in Neurodegenerative Proteinopathies: Polyglutamine Diseases Join the (Mis)Fold," *Am. J. Hum. Genet.*, 64(2): 339-345 (Feb. 1999).

Polpl et al., "Pharmacotherapeutic Biomarker Discovery in a Mouse Model of Amyotrophic Lateral Sclerosis," *Society for Neuroscience Abstract Viewer and Itinerary Planner*, 2002: 1 (Nov. 2002).

Ranganathan et al., "P14 Protein Profiling of Amyotrophic Lateral Sclerosis (ALS) by Mass Spectrometric Analysis," *ALS and other Motor Neuron Disorders*, 3(Supplement 2): 57 (Nov. 2002).

Ranganathan et al., "Alterations in G1 to S Phase Cell-Cycle Regulators During Amyotrophic Lateral Sclerosis," *American Journal of Pathology*, 162(3): 823-835 (Mar. 2003).

Ranganathan et al., "Protein Profiling of Amyotrophic Lateral Sclerosis Patients by Mass Spectrometry," *FASEB Journal*, 17(4-5): 1 (Mar. 2003).

Ranganathan et al. "Proteomic Profiling of Cerebrospinal Fluid Identifies Biomarkers for Amyotrophic Lateral Sclerosis," *Journal of Neurochemistry*, 95(5): 1461-1471 (Dec. 2005).

Rosen et al., "Mutations in Cu/Zn Superoxide Dismutase Gene are Associated with Familial Amyotrophic Lateral Sclerosis," *Nature*, 362(6415): 59-62 (Mar. 4, 1993).

Rosen et al., "Frequent ALA 4 to VAL Superoxide Dismutase-1 Mutation is Associated with a Rapidly Progressive Familial Amyotrophic Lateral Sclerosis," *Human Molecular Genetics*, 3(6): 981-987 (1994).

Rothstein et al., "β-Lactam antibiotics offer neuroprotection by increasing glutamate transporter expression," *Nature*, 433(7021): 73-77 (Jan. 6, 2005).

Shaw et al., "Serum and Cerebrospinal Fluid Biochemical Markers of ALS," *ALS and Other Motor Neuron Disorders, Supp*2: S61-S67 (2000).

Smith et al., "Presence of 4-Hydroxynonenal in Cerebrospinal Fluid of Patients with Sporadic Amyotrophic Lateral Sclerosis," *Annals of Neurology*, 44(4): 696-699 (Oct. 1998).

Sousa et al., "Deposition of Transthyretin in Early Stages of Familial Amyloidotic Polyneuropathy," *American Journal of Pathology*, 159(6): 1993-2000 (Dec. 2001).

Sousa et al., "Evidence for Early Cytotoxic Aggregates in Transgenic Mice for Human Transthyretin Leu55Pro," *American Journal of Pathology*, 161(5): 1935-1948 (Nov. 2002).

Sousa et al., "Neurodegeneration in Familial Amyloid Polyneuropathy: From Pathology to Molecular Signaling," *Progress in Neurobiology*, 71: 385-400 (2003).

Spreux-Varoquaux et al., "Glutamate Levels in Cerebrospinal Fluid in Amyotrophic Lateral Sclerosis: A Reappraisal Using a New HPLC Method with Coulometric Detection in a Large Cohort of Patients," *Journal of the Neurological Sciences*, 193(2): 73-78 (2002).

Stein et al., "Neutralization of Transthyretin Reverses the Neuroprotective Effects of Secreted Amyloid Precursor Protein (APP) in APP$_{sw}$ Mice Resulting in Tau Phosphorylation and Loss of Hippoampal Neurons: Support for the Amyloid Hypothesis," *The Journal of Neuroscience*, 24(35): 7707-7717 (Sep. 1, 2004).

Subramaniam et al., "Mutant SOD1 Causes Motor Neuron Disease Independent of Copper Chaperone-Mediated Copper Loading," *Nature Neuroscience*, 5(4): 301-307 (Apr. 2002).

Tsuzuki et al., "Structure of the Human Prealbumin Gene," *The Journal of biological Chemistry*, 260(22): 12224-12227 (Oct. 5, 1985).

Tsuzuki et al., "Transthyretin Binds Amyloid β Peptides, Aβ1-42 and Aβ1-40 to Form Complex in the Autopsied Human Kidney — Possible Role of Transthyretin for Aβ Sequestration," *Neuroscience Letters*, 281(2/3): 171-174 (2000).

Vinceti et al., "Lead, Cadmium, and Selenium in the Blood of Patients with Sporadic Amyotrophic Lateral Sclerosis," *The Italian Journal of Neurological Sciences*, 18(2): 87-92 (Apr. 2, 1997).

Zheng et al., "Transthyretin, Thyroxine, and Retinol-Binding Protein in Human Cerebrospinal Fluid: Effect of Lead Exposure," *Toxicological Sciences*, 61: 107-114 (2001).

Zheng, "Toxicology of Choroid Plexus: Special Reference to Metal-Induced Neurotoxicities," *Microscopy Research and Technique*, 52: 89-103 (2001).

Zhu et al., "Internal Cleavage of the Inhibitory 7B2 Carboxyl-Terminal Peptide by PC2: A Potential Mechanism for its Inactivation," *Proceedings of the National Academy of Sciences of the United States of America*, 93(10): 4919-4924 (May 1996).

* cited by examiner

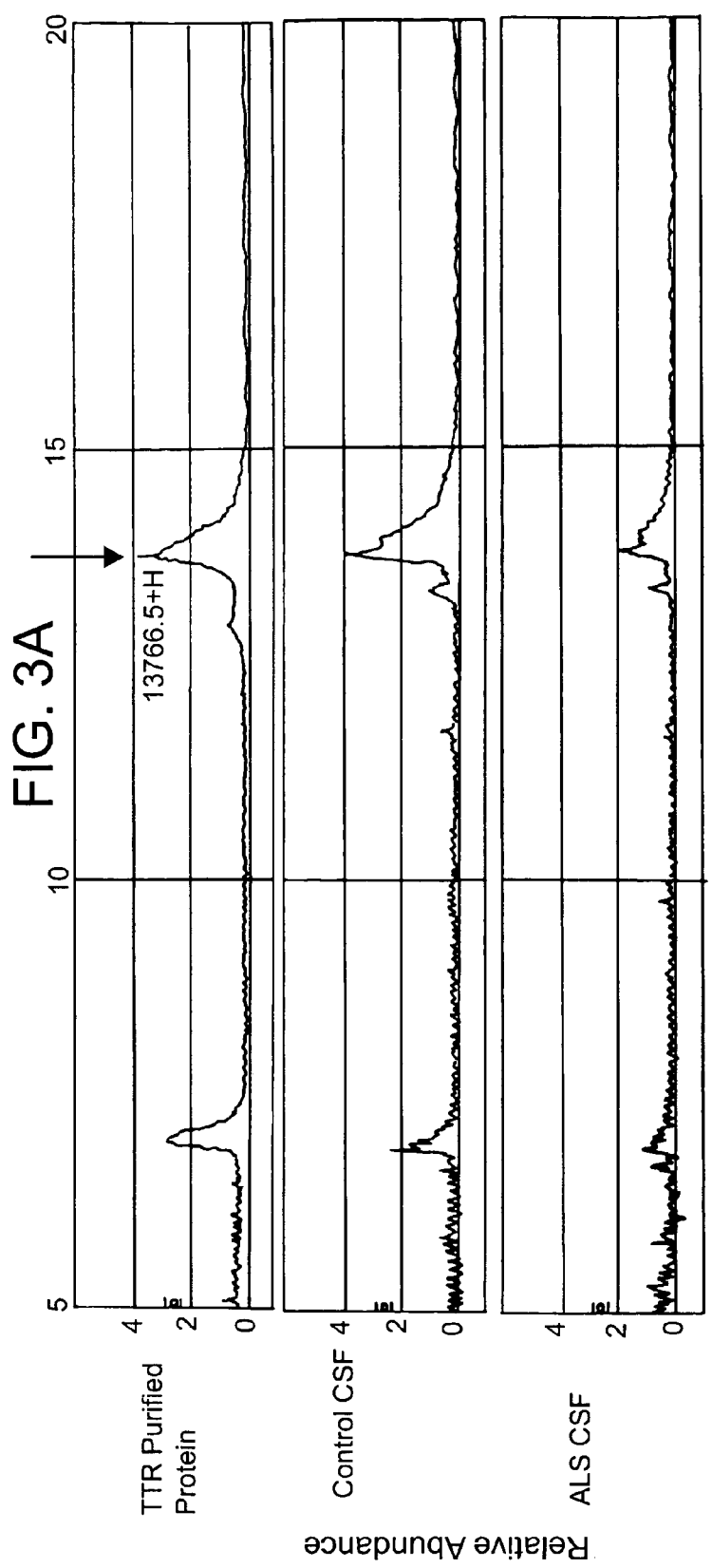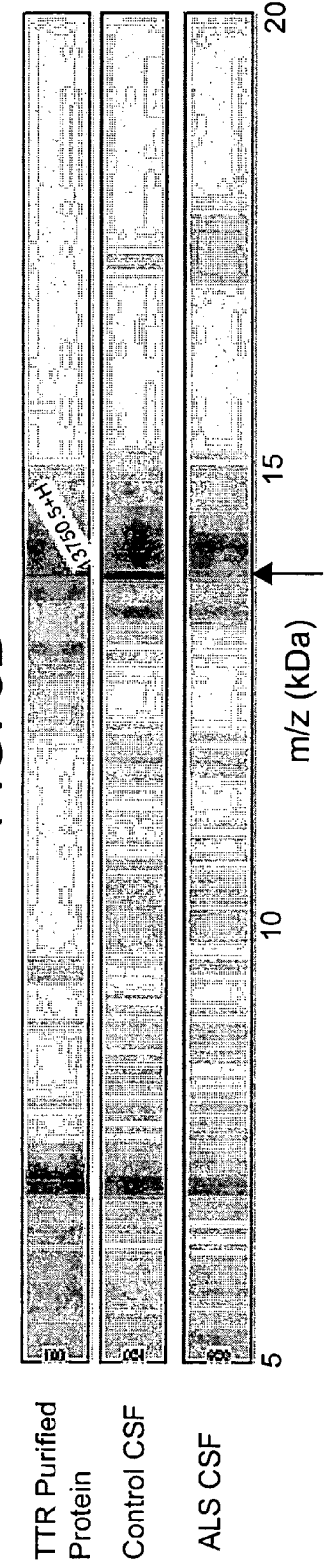

FIG. 7
Patient 1
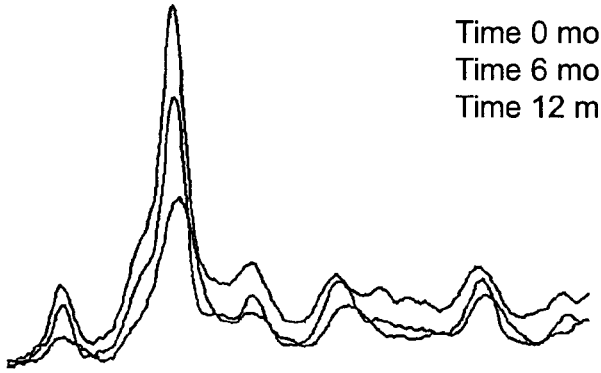
Cystatin C
Time 0 months
Time 6 months
Time 12 months
Patient 2
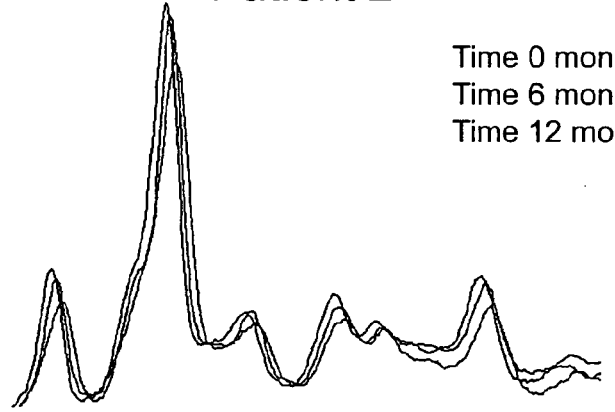
Time 0 months
Time 6 months
Time 12 months
Patient 3
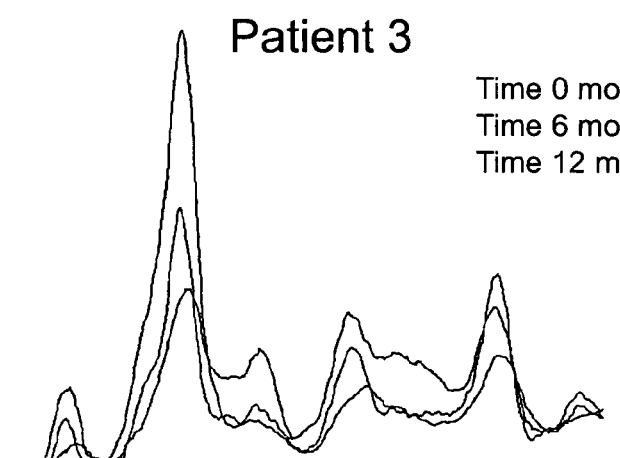
Time 0 months
Time 6 months
Time 12 months
Molecular Mass (kDa)
Relative Intensity

SEQUENCE LISTING

```
<160> NUMBER OF SEQ ID NOS: 4

<210> SEQ ID NO 1
<211> LENGTH: 636
<212> TYPE: DNA
<213> ORGANISM: Homo sapiens
<220> FEATURE:
<221> NAME/KEY: misc_feature
<222> LOCATION: (1)..(636)
<223> OTHER INFORMATION: 7b2 cDNA

<400> SEQUENCE: 1
gcaactgttt tgtttaatac ctttctgcaa tgatgctctg cctagcatgg aaacttaaga      60
caaaagcaac ctcctaagga ttctttgtta caacccctt ctgggtggtc ctcgaaccac      120
aacctggagt ggttgcatca ttataattgt attatcacaa ttgccgattg tagcctatca     180
gtatacattt ggtcttttat ctgcaggttg acaatggtct ccaggatggt ctctaccatg     240
```

```
ctatctggcc tactgttttg gctggcatct ggatggactc cagcatttgc ttacagcccc      300
cggacccctg accgggtctc agaagcagat atccagaggc tgcttcatgg tgttatggag      360
caattgggca ttgccaggcc ccgagtggaa tatccagctc accaggccat gaatcttgtg      420
ggcccccaga gcattgaagg tatttactgt gttctgatgg tttgaagttt ccgttagcat      480
tttaaataat atatttgcac acttctcaca acaaccttat aagtagatgc ctttattatc      540 ctatttttt cagaggagga agctaatttt taagagactc tactttctca tggttttccc      600
tttcttcttc tacacagtgt ctacatactt acatat                               636
```

```
<210> SEQ ID NO 2
<211> LENGTH: 211
<212> TYPE: PRT
<213> ORGANISM: Homo sapiens
<220> FEATURE:
<221> NAME/KEY: MISC_FEATURE
<222> LOCATION: (1)..(211)
<223> OTHER INFORMATION: 7b2

<400> SEQUENCE: 2
```

```
Met Val Ser Arg Met Val Ser Thr Met Leu Ser Gly Leu Leu Phe Trp
 1               5                  10                  15

Leu Ala Ser Gly Trp Thr Pro Ala Phe Ala Tyr Ser Pro Arg Thr Pro
            20                  25                  30

Asp Arg Val Ser Glu Ala Asp Ile Gln Arg Leu Leu His Gly Val Met
        35                  40                  45

Glu Gln Leu Gly Ile Ala Arg Pro Arg Val Glu Tyr Pro Ala His Gln
    50                  55                  60

Ala Met Asn Leu Val Gly Pro Gln Ser Ile Glu Gly Gly Ala His Glu
65                  70                  75                  80

Gly Leu Gln His Leu Gly Pro Phe Gly Asn Ile Pro Asn Ile Val Ala
                85                  90                  95

Glu Leu Thr Gly Asp Asn Ile Pro Lys Asp Phe Ser Glu Asp Gln Gly
            100                 105                 110

Tyr Pro Asp Pro Pro Asn Pro Cys Pro Val Gly Lys Thr Asp Asp Gly
        115                 120                 125

Cys Leu Glu Asn Thr Pro Asp Thr Ala Glu Phe Ser Arg Glu Phe Gln
    130                 135                 140

Leu His Gln His Leu Phe Asp Pro Glu His Asp Tyr Pro Gly Leu Gly
145                 150                 155                 160

Lys Trp Asn Lys Lys Leu Leu Tyr Glu Lys Met Lys Gly Gly Glu Arg
                165                 170                 175

Arg Lys Arg Arg Ser Val Asn Pro Tyr Leu Gln Gly Gln Arg Leu Asp
            180                 185                 190

Asn Val Val Ala Lys Lys Ser Val Pro His Phe Ser Asp Glu Asp Lys
        195                 200                 205

Asp Pro Glu
    210
```

```
<210> SEQ ID NO 3
<211> LENGTH: 482
<212> TYPE: DNA
<213> ORGANISM: Homo sapiens
<220> FEATURE:
<221> NAME/KEY: misc_feature
<222> LOCATION: (1)..(482)
<223> OTHER INFORMATION: cystatin C cDNA

<400> SEQUENCE: 3
```

```
ttccgaaaa gggagtgcag ggcccggggg ggtggggcgg cgaaggcggg aagggataaa      60
accgcagtcg ccggcctcgc ggggctcacg gcctcgcctc ggtatcgccg cgggtcctct    120
ctatctagct ccagcctctc gcctgcgccc cactccccgc gtcccgctcc tagccgacca    180
tggccgggcc cctgcgcgcc ccgctgctcc tgctggccat cctggccgtg gccctggccg    240
tgagccccgc gaccggctcc agtcccggca agccgccgcg cctggtggga ggccccatgg    300
acgccagcgt ggaggaggag ggtgtgcggc gtgcactgga ctttgccgtc ggcgagtaca    360
acaaagccag caacgacatg taccacagcc gcgcgctgca ggtggtgcgc gcccgcaagc    420
aggtgcgtgc cgcccccgc aggtccgaag ccccggcccc gccgtcccag cctccccccg    480
cg                                                                   482
```

```
<210> SEQ ID NO 4
<211> LENGTH: 146
<212> TYPE: PRT
<213> ORGANISM: Homo sapiens
<220> FEATURE:
<221> NAME/KEY: MISC_FEATURE
<222> LOCATION: (1)..(146)
<223> OTHER INFORMATION: cystatin C

<400> SEQUENCE: 4

Met Ala Gly Pro Leu Arg Ala Pro Leu Leu Leu Ala Ile Leu Ala
 1               5                  10                  15

Val Ala Leu Ala Val Ser Pro Ala Thr Gly Ser Ser Pro Gly Lys Pro
                20                  25                  30

Pro Arg Leu Val Gly Gly Pro Met Asp Ala Ser Val Glu Glu Glu Gly
            35                  40                  45

Val Arg Arg Ala Leu Asp Phe Ala Val Gly Glu Tyr Asn Lys Ala Ser
        50                  55                  60

Asn Asp Met Tyr His Ser Arg Ala Leu Gln Val Val Arg Ala Arg Lys
 65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
            115                 120                 125

Ala Val Pro Trp Gln Gly Thr Met Thr Leu Ser Lys Ser Thr Cys Gln
        130                 135                 140

Asp Ala
145
```

MODULATION OF THE NEUROENDOCTRINE SYSTEM AS A THERAPY FOR MOTOR NEURON DISEASE

CROSS-REFERENCE TO RELATED APPLICATIONS

This patent application claims the benefit of U.S. Provisional Patent Application No. 60/632,450, filed Dec. 2, 2004.

STATEMENT REGARDING FEDERALLY SPONSORED RESEARCH AND DEVELOPMENT

This invention was made in part with Government support under Grant Number ES013469 awarded by the National Institute of Environmental Health Sciences. The Government may have certain rights in this invention.

BACKGROUND OF THE INVENTION

Amyotrophic lateral sclerosis (ALS), also known as Lou Gehrig's disease or motor neuron disease (MND), is one of several neurodegenerative diseases of the central nervous system. ALS is the most common adult onset motor neuron disease, affecting one in every 20,000 individuals, with an average age of onset of 50-55 years. ALS is characterized by rapidly progressive degeneration of motor neurons in the brain, brainstem, and spinal cord (Cleveland, 2001). The median survival of patients from time of diagnosis is five years.

ALS exists in both sporadic and familial forms. Familial ALS (FALS) comprises only 5-10% of all ALS cases. Over the last decade, a number of basic and clinical research studies have focused on understanding the familial form of the disease, which has led to the identification of eight genetic mutations related to FALS. Transgenic mice expressing point mutants of the Cu/Zn superoxide dismutase-1 (SOD1) gene develop an age-dependent progressive motor weakness similar to human ALS due to a toxic gain of function (Rosen, 1993; Rosen, 1994; Borchelt, 1994).

These genetic mutations, however, do not explain sporadic ALS (SALS). The pathogenesis of SALS is multifactorial. A number of different model systems, including SOD1 transgenic mice, in vitro primary motor neuron cultures or spinal cord slice cultures, in vivo imaging studies, and postmortem examination of tissue samples, have been utilized to understand the pathogenesis of ALS (Subramaniam, 2002); Nagai, 2001; Menzies, 2002; Kim, 2003; Ranganathan, 2003). Although these studies have yielded therapeutic targets and several clinical trials, there are no drugs that delay disease onset or prolong long-term survival of ALS patients. Riluzole (Rilutek®, Aventis), a glutamate antagonist, currently is the only FDA-approved medication available to treat ALS. Riluzole, however, extends life expectancy by only a few months (Miller, 2003). Creatine and a-tocopherol have shown some efficacy in relieving the symptoms of ALS in SOD1 transgenic mice, but exhibit minimal efficacy in human ALS patients (Groeneveld, 2003; Desnuelle, 2001).

Studies have been performed which have identified early protein biomarkers for ALS, using mass spectrometry based proteomics of cerebrospinal fluid (CSF) and spinal cord samples of human subjects (see U.S. Patent Application 10/972,732, published as US 2005-0148026 A1, the disclosure of which is incorporated herein). For example, three neuroendocrine proteins (transthyretin, 7B2, and cystatin C) that exhibit alterations early in the disease pathogenesis in humans were identified in a proteomics analysis.

Transthyretin regulates thyroid function and retinoic acid signaling in the brain by binding T4 and retinol-binding protein, respectively, and binds other proteins including the amyloid beta peptide (Aβ) to help sequester and prevent amyloid deposition (Palha, 2002; Bernstein, 2002; Tsuzuki, 2000). Retinoic acid signaling is an important component of neural plasticity and regeneration, and absence of retinoids can induce motor neuron disease in rats and decreased retinoid signaling has been observed in sporadic ALS patients (Mey, 2004; Corcoran, 2002).

Transthyretin (TTR) is a protein made by motor neurons in the spinal cord and choroid plexus cells that line the ventricles of the nervous system and produce the CSF. Transthyretin regulates thyroid function and retinoic acid signaling in the brain by binding T4 and retinol-binding protein, respectively, and binds other proteins including the amyloid beta peptide (Aβ) to help sequester and prevent amyloid deposition (Palha, 2002; Bernstein, 2002; Tsuzuki, 2000). T4 is a critical component of thyroid function and can also function to impede cell cycle progression and induce cell differentiation. Direct administration of T4 into a transgenic model for multiple sclerosis enhances remyelination and is neuroprotective for axonal pathology (Fernandez et al, 2004). Retinoic acid is a known antioxidant, and oxidative injury is one proposed mechanism for motor neuron cell death in ALS. Decreased levels of TTR also have been associated with increased brain levels of metals such as lead in the nervous system and metal toxicity induced neurodegeneration (Zheng et al., 2001). TTR also has been recently reported to have direct neuroprotective functions in neurons. The addition of TTR to neurons was found to be protective to the addition of the Aβ peptide that accumulates during Alzheimer's disease (AD) (Stein et al., 2004). Injection of inhibitory antibodies to TTR into a transgenic animal model for AD results in the loss of neuroprotective functions of TTR and acceleration of the disease process (Stein et al., 2004). Thus, the loss of TTR function hastened disease pathogenesis in an animal model of a neurodegenerative disease. Finally, genetic variants of TTR cause transthyretin-associated hereditary amyloidosis (ATTR) in which amyloid accumulates in various tissues and organs (Bergen et al, 2004). ATTR is most common between the third and seventh decades of life, similar to that of ALS. During ALS, it is likely that reduced CSF levels of TTR result in altered transport of T4 and retinol/vitamin A, thus altering thyroid function and increasing oxidative stress. It is also probable that reduced TTR levels in motor neurons decrease neuroprotective functions and increase oxidative stress in motor neurons, thus enhancing neurodegeneration. In addition, TTR genetic variants may increase susceptibility of individuals to develop ALS or hasten disease pathogenesis.

Transthyretin (TTR) variants can be identified by mass spectrometry and verified by gene sequencing. For the mass spectrometry, TTR first is purified from a human sample by affinity chromatography using anti-TTR antibody. The purified TTR is reduced using tris(2-caroxyethyl)phosphine (TCEP) and then analyzed by mass spectrometry to resolve differences in the protein mass indicative of a polymorphism in the TTR gene resulting in an altered amino acid. The most common variants (denoted as wildtype amino acid, location within the protein, and mutant amino acid) are Val30Met and Gly6Ser, though over 100 variants are known (see, e.g., Connors, 2003). Specific mass shifts observed by mass spectrometry are indicative of gene polymorphisms. Samples containing such variant proteins can be analyzed by DNA sequencing to confirm the mass spectrometry results. TTR genetic variants may increase susceptibility to developing ALS due to environmental exposures.

Recent studies have shown that transthyretin functions as a neuroprotective protein and injection of transthyretin protein reduces amyloid deposition and cognitive decline in an animal model of Alzheimer's disease (Stein, 2004). Transthyretin protein levels are reduced by exposure to heavy metals and other toxins (Zheng, *Toxicol. Sci.,* 2001; Zheng, *Microscopy Res. & Tech.,* 2001). Environmental exposure to lead and other heavy metals has been proposed as a risk factor in the etiology of ALS (Vinceti, 1997; Kamel, 2002). Genetic variants of transthyretin decrease protein function and cause a familial form of polyneuropathy (Benson, 1985). ALS subjects that have transthyretin genetic variants that decrease transthyretin function will make the individual at increased risk for developing ALS, thus suggesting that transthyretin is a novel risk or susceptibility factor for ALS. It is likely that the transthyretin plays a role in motor neuron survival and genetic polymorphisms and/or decreased expression levels make neurons more susceptible to injury or toxin exposure. This could help explain the increased incidence of ALS in Gulf War Veterans deployed to specific active zones noted above. TTR protein may also directly participate in motor neuron degeneration by generating extracellular or intracellular toxic protein aggregates. TTR fibrils have been observed in familial polyneuropathies induced by TTR mutations (Sousa, 2003). In vitro studies have shown that the toxic form of TTR is the non-fibrillar protein aggregates and that fully formed TTR containing fibrils is non-toxic (Sousa, 2001; Sousa, 2002). Therefore the presence of non-fibrillar TTR protein aggregates in ALS spinal cord tissue will be interpreted as directly contributing to motor neuron degeneration. These experiments provide novel data implicating TTR and TTR functional pathways in motor neuron survival and highlight new pathogenic mechanisms for ALS. Reduced TTR function, either by genetic polymorphisms or post-translational modifications that alter protein function or by reduced expression levels during ALS, may directly induce motor neuron cell loss since the loss of retinoid signaling can induce motor neuron disease in rodents (Corcoran, 2002).

The second neuroendocrine protein is 7B2 (Martens, 1989). It has been determined that 7B2 protein alterations occur during ALS. More specifically, in ALS subjects increased levels of a carboxy-terminal fragment of 7B2 referred to as 7B2CT were observed. 7B2 is a neuroendocrine secretory protein that functions as a chaperone for the pro-protein convertase 2 protein (PC2). 7B2 binds to PC2 in the endoplasmic reticulum and facilitates its transport to other compartments of the secretory pathway where it is proteolytically matured and activated (Mbiday, 2001). PC2 participates in the production and secretion of numerous hormones and neuropeptides, including neuropeptide Y, somatostatin, galanin, and vasopressin. A prior study has shown expression of 7B2 in motor neurons and in the spinal cord. 7B2 also acts as a chaperone protein for the maturation and secretion of insulin-like growth factor 1 (IGF-1), which is currently in trials as a therapy for ALS (Chaudhuri, 1995). 7B2 is processed by the enzyme furin to form a carboxy-terminal fragment called 7B2CT that functions as an inhibitor of PC2 activation. Carboxypeptidase E cleaves 7B2CT for its degradation. Furin and/or carboxypeptidase E activity may also be altered in ALS subjects. Therefore increased levels of 7B2CT in the CSF of ALS subjects may indicate that PC2 activation is reduced in multiple cell types of the nervous system, including motor neurons. This implies that maturation and secretion of many neuroendocrine peptides, growth factors and hormones is reduced in ALS.

The third neuroendocrine protein identified is cystatin C (Abrahamson, 1990). Cystatin C has been identified using mass spectrometry as a diagnostic biomarker for ALS. CSF and lumbar spinal cord tissue samples from ALS subjects exhibit less cystatin C than control subjects. Cystatin C is a secreted protein that functions both as a cysteine protease inhibitor and can function as an autocrine or paracrine factor in neurogenesis of neural stem cells. Mutations in the cystatin C gene cause a rare disease called hereditary brain amyloid angiopathy, and increased levels of cystatin C have been found in other neurodegenerative diseases including Alzheimer's disease, ischemia, and Creutzfeldt-Jakob disease (CJD). Decreased levels of cystatin C in the CSF of ALS subjects or altered post-translational modifications to cystatin C suggest decreased levels of protease inhibitors, which may contribute to disease pathogenesis.

Despite the identification of early protein biomarkers for ALS, there remains a need, however, for improved methods for identifying therapeutic targets of ALS, and improved methods of diagnosing and monitoring the progress of the disease.

BRIEF SUMMARY OF THE INVENTION

The invention provides a method for treating amyotrophic lateral sclerosis (ALS) in a subject.

The invention also provides a method for determining the susceptibility of a subject to developing ALS. The method comprises (a) obtaining a sample from the subject, (b) isolating from the sample a nucleic acid molecule encoding the transthyretin protein, and (c) determining the amino acid or nucleotide sequence of the protein, wherein a protein or nucleic acid molecule encoding a variant of the transthyretin protein indicates that the subject is susceptible to developing ALS.

In addition, the invention provides a method for determining progression of ALS in a subject. The method comprises (a) obtaining a sample from the subject, (b) isolating from the sample a transthyretin protein, (c) analyzing the transthyretin protein from the sample by mass spectroscopy, and (d) determining a mass spectral profile for the sample, wherein the presence of a variant of a wild type transthyretin protein in the sample indicates progression of ALS in the animal.

The invention also provides a method for determining progression of ALS in a subject. The method comprises (a) obtaining a sample from the subject, (b) isolating from the sample a transthyretin or cystatin C protein, (c) analyzing the transthyretin or cystatin C protein levels from the sample, and (d) comparing the protein levels to transthyretin or cystatin C protein levels obtained from the same subject at an earlier time, wherein a change in the protein levels indicates progression of ALS in the subject.

BRIEF DESCRIPTION OF THE SEVERAL VIEWS OF THE DRAWINGS

FIG. 3 presents data demonstrating the presence of TTR (transthyretin) monomer in ALS via immuno-SELDI-TOF-MS. Panel A depicts a representative SELDI spectra of purified human TTR protein (positive control), control CSF, and ALS CSF samples. Purified anti-TTR antibody was bound to the protein chip surfaces and individual samples were added to measure the level of TTR protein. Seven control and seven ALS subjects were tested using these antibody containing chips. The arrow indicates the presence of the 13.78 kDa TTR monomer. The two-fold difference in the relative peak intensity values for the 13.78 kDa peak between control and ALS subjects was significantly significant ($p=0.02$). Panel B depicts a ciphergen-based software assisted gel view of the spectra represented in panel A.

FIG. 7 presents data demonstrating decreases in the mass spectral peak for either cystatin C or transthyretin over a 12 or 15-month time frame within individual ALS subjects.

DETAILED DESCRIPTION OF THE INVENTION

Figure 1:
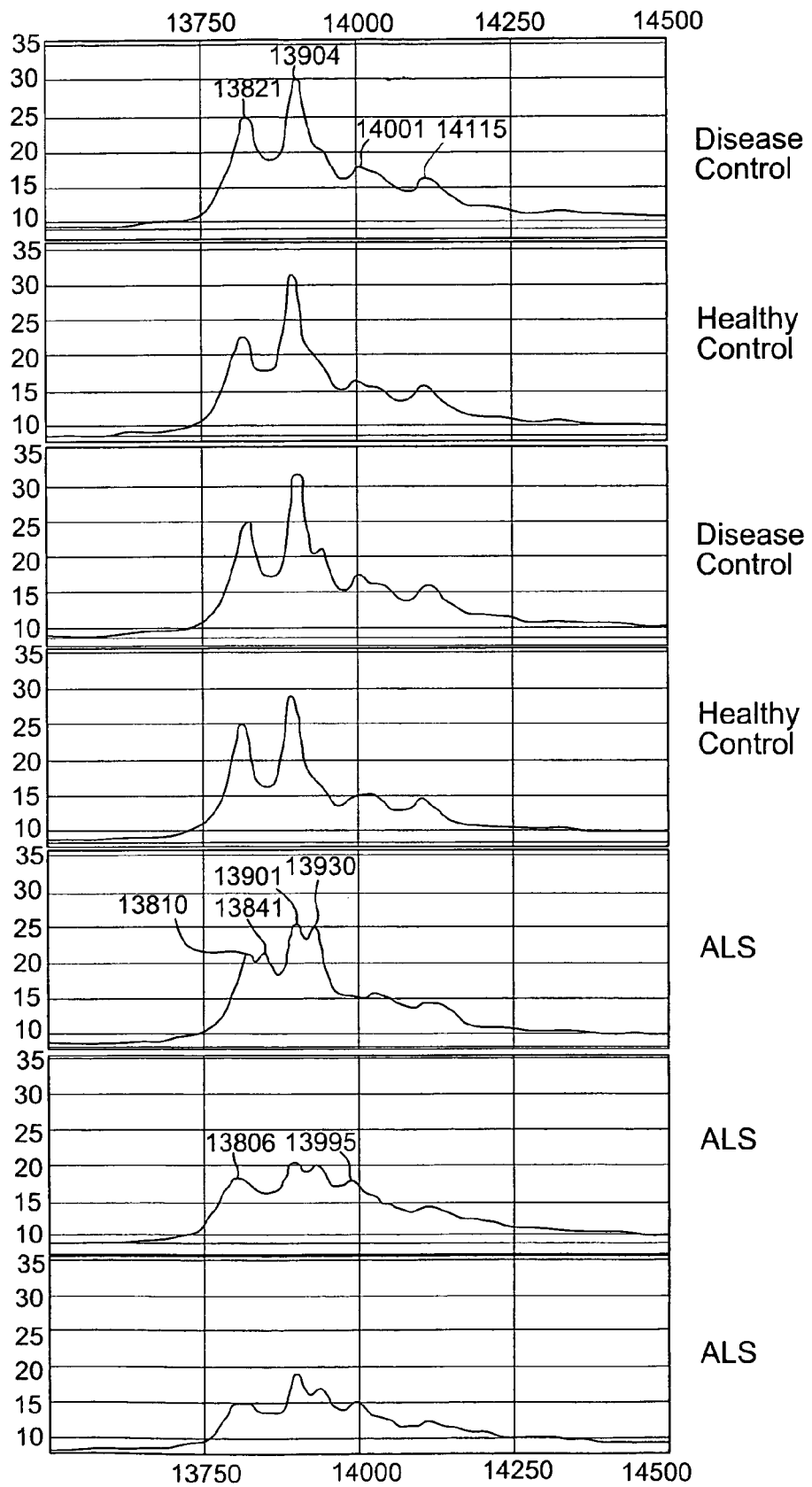
FIG. 1 presents data demonstrating transthyretin mass shifts in ALS patients. Mass spectral analysis of CSF from healthy and disease controls are shown in the top 4 panels, and mass spectral analysis from ALS subjects are shown in the bottom 3 panels. The mass region containing TTR is shown for each sample (mass region between 13,500 to 14,500 Daltons). The control subjects (both healthy and neurologic disease controls) exhibit similar TTR profiles, whereas the ALS subjects exhibit mass shifts and the presence of TTR mass doublets that were observed in approximately 30% of ALS subjects. Molecular mass (Da) is shown for the major TTR peaks for the healthy and other neurologic disease control subjects (top panel). TTR protein peaks in ALS patients often exhibit a 30-Da mass shift (13810→13841; 13901→13930) as shown in the third panel from the bottom.

In one aspect, the present invention provides a method for treating amyotrophic lateral sclerosis (ALS) in a subject or for prophylaxis thereof within the subject. In accordance with this aspect, an anti-ALS-effective amount of a composition comprising either a thyroxine protein, a transthyretin protein, a 7B2 protein, an inhibitor of an enzyme that processes a 7B2 protein, a cystatin C protein, cysteine protease inhibitor, a neuroendocrine protein, or combinations thereof (or, in some embodiments, a gene transfer vector encoding the same) is administered to the subject in an amount, at a location, and for a time course sufficient to treat ALS within the subject. Preferably, the desired factor is administered to the nervous system of the subject, which is particularly preferred where the factor is a thyroxine.

The "subject" can be any suitable animal, but preferably is a mammal, such as a mouse, rat, monkey, or human. It is contemplated that the aforementioned inventive method can be used to treat ALS in animal models of the disease, in which case the subject is a non-human animal (e.g., a mouse, rat, monkey, dog, etc.). In a preferred embodiment, the subject is a human suffering from ALS.

For treatment of ALS in a subject, following introduction of the composition into the subject in accordance with the inventive method, the subject's condition is monitored to assess the severity of ALS. Suitable application of the inventive method will result in slowing of the progression of ALS and, in preferred embodiments, result in plateauing of the progress of the disease. Indeed, in more preferred embodiments, application of the inventive method will result in a reduction of the symptoms associated with ALS in the subject or even in substantial or complete remission of ALS. Thus, while the inventive method can lead to a cure of ALS in some subjects, any degree of improvement in the prognosis of the subject following application of the inventive method is considered to be successful application. Moreover, it is to be understood that the inventive method can be used as monotherapy or adjunctively in combination with other therapeutic agents (e.g., riluzole) or therapeutic methods.

For prophylaxis, following introduction of the composition into the subject, the subject is suitably monitored to assess the development of ALS and/or continued risk of developing ALS. Successful prophylaxis can be measured by the absence of ALS in the subject for longer than the initial assessment of risk had predicted.

The desired factor (e.g., protein, therapeutic fragment, or pharmacologic mimic, or gene transfer vector) can be prepared by methods known to those of ordinary skill in the art. For example, the protein or fragment can be synthesized using solid phase peptide synthesis techniques (e.g., Fmoc). Alternatively, the factor can be synthesized using recombinant DNA technology (e.g., using bacterial or eukaryotic expression systems). Accordingly, to facilitate such methods, where the factor is a protein or fragment thereof, the invention provides genetic vectors (e.g., plasmids) comprising a sequence encoding the factor, as well as host cells comprising such vectors. Methods for solid state protein synthesis and recombinant protein synthesis are well-known in the art. For example, "Molecular Cloning, A Laboratory Manual" (Sambrook et al., 3d Ecition, Cold Spring Harmor Press), is a well-known reference detailing many suitable techniques for recombinant production of polypeptides. Accordingly, the invention provides the protein or fragment in recombinant form. Alternatively a protein or fragment can be isolated from any species as described herein. In addition, the pharmacological mimic can be prepared as described above, or it can be synthesized using appropriate organic synthesis methods, which are well known to those of ordinary skill in the art.

However it is made, a protein, fragment, or mimic can be isolated and/or purified (or substantially isolated and/or substantially purified). Accordingly, the invention provides the protein, fragment, or mimic in substantially isolated form (i.e., substantially isolated from other polypeptides or impurities). The protein, fragment, or mimic can be isolated from other proteins as a result of solid phase protein synthesis, for example. Alternatively, the protein, fragment, or mimic can be substantially isolated from other proteins after cell lysis from recombinant production. Standard methods of protein purification (e.g., HPLC) can be employed to substantially purify the protein, fragment, or mimic. Thus, a preparation of the protein, fragment, or mimic preferably is at least 90% free of other proteins and/or contaminants, and more preferably is at least about 95% free of other proteins and/or contaminants (such as at least about 97% or 98% free of other proteins and/or contaminants). In a most preferred embodiment, the invention provides a preparation of the protein, fragment, or mimic that is greater than 99% free of other proteins and/or contaminants (e.g., greater than 99.5% or even 99.9% or even 99.99% free of other proteins).

In another embodiment, the invention provides a preparation of the protein, fragment, or mimic in a number of formulations, depending on the desired use. For example, where the protein, fragment, or mimic is substantially isolated (or even nearly completely isolated from other proteins), it can be formulated in a suitable medium solution for storage (e.g., under refrigerated conditions or under frozen conditions). Such preparations can contain protective agents, such as buffers, preservatives, cryprotectants (e.g., sugars such as trehalose), etc. The form of such preparations can be solutions, gels, etc., and the protein can, in some embodiments, be prepared in lyophilized form. Moreover, such preparations can include other desired agents, such as small molecules or even other proteins or peptides, if desired. Indeed, the invention provides such a preparation comprising a mixture of different embodiments of the protein, fragment, or mimic (e.g., a plurality of species as described herein). Technology for preparing such compositions (e.g., lyophilization, preparation of protein solutions, etc.), is within the state of the art.

In accordance with this aspect of the inventive method, the composition administered to the subject can comprise, consist of, or consist essentially of a desired protein or a therapeutic fragment or pharmacologic mimic thereof, and preferably also a pharmaceutically acceptable carrier. Any carrier which can supply the protein, fragment, or mimic without destroying the protein, fragment, or mimic within the carrier is a suitable carrier, and such carriers are well known in the art. The composition can be formulated for parenteral, oral, or topical administration. For example, a parenteral formulation could consist of a prompt or sustained release liquid preparation, dry powder, emulsion, suspension, or any other standard formulation. An oral formulation of the composition could be, for example, a liquid solution, such as an effective amount of the composition dissolved in diluents (e.g., water, saline, juice, etc.), suspensions in an appropriate liquid, or suitable emulsions. An oral formulation could also be delivered in tablet form, and could include excipients, colorants, diluents, buffering agents, moistening agents, preservatives, flavoring agents, and pharmacologically compatible excipients. A topical formulation could include compounds to enhance absorption or penetration of the active ingredient through the skin or other affected areas, such as dimethylsulfoxide and related analogs. The composition could also be delivered topically using a transdermal device, such as a patch, which could include the composition in a suitable solvent system with an adhesive system, such as an acrylic emulsion, and a polyester patch.

In one embodiment of this aspect of the invention, the method comprises, consists of, or consists essentially of administering to the nervous system of the subject a composition comprising a thyroxine protein or a therapeutic fragment or pharmacologic mimic thereof. Preferably, the composition also includes a pharmaceutically acceptable carrier. The composition can comprise, consist or, or consist essentially of any protein identified or characterized as a thyroxine protein. The protein can be synthetic or can be isolated from any species (e.g., human). In a preferred embodiment, the amino acid sequence of the protein is identical or substantially similar (e.g. at least about 80%, at least about 90%, or at least about 95% identical) to the full length human thyroxine protein. For example, the protein may contain substitutions of one or more amino acid residues for an amino acid other than the indicated residue. The substitution can be, but need not be, a conservative substitution. Conservative substitutions are well known in the art and can be amino acid replacements that preserve the structure and functional properties of proteins, such as the substitution of one or more amino acids by similar amino acids. For example, a conservative substitution can be the substitution of an amino acid for another amino acid within the same general class (e.g., an acidic amino acid, a basic amino acid, or a neutral amino acid). In another embodiment, the composition comprises, consists or, or consists essentially of a therapeutic fragment of a thyroxine protein. A therapeutic fragment is any fragment that has an effect on a subject with ALS as described above. The fragment can have any suitable amino acid sequence and can be of any length. For example, the fragment can have an amino acid sequence identical to a portion of the human protein, or it can be substantially similar to a portion of the human protein (e.g., at least about 80%, at least about 90%, or at least about 95% identical). In another embodiment the composition comprises, consists or, or consists essentially of a pharmacologic mimic of a thyroxine protein. A pharmacological mimic can be any molecule or composition that simulates the role of a thyroxine protein (e.g. thyroid function) or the effect of a thyroxine protein on a subject with ALS.

In another embodiment of this aspect, the method comprises, consists of, or consists essentially of modulation of the neuroendocrine system to increase endogenous transthyretin gene expression or to directly add transthyretin to provide neuroprotective functions in ALS patients. Preferably, the method comprises administering to the subject a composition comprising a transthyretin protein or a therapeutic fragment or pharmacologic mimic thereof. Preferably, the composition also includes a pharmaceutically acceptable carrier. The inventive method is performed substantially as described above. Alternatively, the protein can be administered to a subject using a gene transfer vector. Any suitable vector can be used such as viral (e.g., adenovirus or lentivirus) or non-viral vectors, and such vectors are well known in the art. The transthyretin protein is encoded by a nucleic acid sequence and can be linked to a promoter. A promoter can be any element which drives production of the protein.

The transthyretin protein can be any protein identified or characterized as a transthyretin protein. The protein can be synthetic or can be isolated from any species (e.g., human). In a preferred embodiment, the amino acid sequence of the protein is identical or substantially similar (e.g. at least about 80%, at least about 90%, or at least about 95% identical) to the full length human transthyretin protein. For example, the protein may contain substitutions of one or more amino acid residues for an amino acid other than the indicated residue. The substitution can be, but need not be, a conservative substitution. The nucleic acid sequence of the protein can be any appropriate sequence given the redundancy of the genetic code. In another embodiment, the protein is a therapeutic fragment of a transthyretin protein. A therapeutic fragment is any fragment that has an effect on a subject with ALS as described above. The fragment can have any suitable amino acid sequence and can be of any length. For example, the fragment can have an amino acid sequence identical to a portion of the human protein, or it can be substantially similar to a portion of the human protein (e.g., at least about 80%, at least about 90%, or at least about 95% identical). In another embodiment the protein or composition is a pharmacologic mimic of a transthyretin protein. A pharmacological mimic can be any molecule or composition that simulates the role of a transthyretin protein (e.g. thyroxine transport) or the effect of a transthyretin protein on a subject with ALS.

In another embodiment of this aspect of the invention, the method comprises administering to the subject a 7B2 protein or a therapeutic fragment or pharmacologic mimic thereof. Preferably, the composition also includes a pharmaceutically acceptable carrier. The inventive method is performed substantially as described above. The 7B2 protein can be any protein identified or characterized as a 7B2 protein (an example of which is disclosed in emb1 locus HSA290438, accession AJ290438.1; see also accession no. CAB90397, SEQ ID NOs: 1 and 2). The protein can be synthetic or can be isolated from any species (e.g., human). In a preferred embodiment, the amino acid sequence of the protein is identical or substantially similar (e.g. at least about 80%, at least about 90%, or at least about 95% identical) to the full length human 7B2 protein. For example, the protein may contain substitutions of one or more amino acid residues for an amino acid other than the indicated residue. The substitution can be, but need not be, a conservative substitution. The nucleic acid sequence of the protein can be any appropriate sequence given the redundancy of the genetic code. In another embodiment, the protein is a therapeutic fragment of a 7B2 protein. A therapeutic fragment is any fragment that has an effect on a subject with ALS as described above. The fragment can have any suitable amino acid sequence and can be of any length. For example, the fragment can have an amino acid sequence identical to a portion of the human protein, or it can be substantially similar to a portion of the human protein (e.g., at least about 80%, at least about 90%, or at least about 95% identical). In another embodiment the protein or composition is a pharmacologic mimic of a 7B2 protein. A pharmacological mimic can be any molecule or composition that simulates the role of a 7B2 protein (e.g. proprotein convertase 2 transport) or the effect of a 7B2 protein on a subject with ALS.

In another embodiment of this aspect of the invention, the inventive method comprises administering to the subject an inhibitor of an enzyme that processes a 7B2 protein. The inventive method is performed substantially as described above. The inhibitor can be any molecule that decreases or abolishes the activity of an enzyme that processes a 7B2 protein, such as a competitive or non-competitive inhibitor. The enzyme can be any enzyme involved in the processing (e.g., synthesis, modification, or transport) of a 7B2 protein. For example, the inhibitor can be furin, carboxypeptidase E, or a combination thereof (see Paquet, 1994; Zhu, 1996).

In another embodiment of this aspect of the invention, the inventive method comprises administering to the subject a cystatin C protein or a therapeutic fragment or pharmacologic mimic thereof. Preferably, the composition also includes a pharmaceutically acceptable carrier. The inventive method is performed substantially as described above. The cystatin C protein can be any protein identified or characterized as a cystatin C protein (see, e.g., emb1 locus HSCST3G, accession X52255.1, emb1 locus HSCYSTC1, accession X61681.1, emb1 locus HSCYSTCR, accession X05607.1, locus HUMCYS3A1 accession M27889.1, UniProtKB/Swiss-Prot:P01034, SEQ ID NOs: 3 and 4). The protein can be synthetic or can be isolated from any species (e.g., human). In a preferred embodiment, the amino acid sequence of the protein is identical or substantially similar (e.g. at least about 80%, at least about 90%, or at least about 95% identical) to the full length human cystatin C protein. For example, the protein may contain substitutions of one or more amino acid residues for an amino acid other than the indicated residue. The substitution can be, but need not be, a conservative substitution. The nucleic acid sequence of the protein can be any appropriate sequence given the redundancy of the genetic code. In another embodiment, the protein is a therapeutic fragment of a cystatin C protein. A therapeutic fragment is any fragment that has an effect on a subject with ALS as described above. The fragment can have any suitable amino acid sequence and can be of any length. For example, the fragment can have an amino acid sequence identical to a portion of the human protein, or it can be substantially similar to a portion of the human protein (e.g., at least about 80%, at least about 90%, or at least about 95% identical). In another embodiment the protein or composition is a pharmacologic mimic of a cystatin C protein. A pharmacological mimic can be any molecule or composition that simulates the role of a cystatin C protein (e.g., cysteine protease inhibition, autocrine or paracrine factors in neurogenesis of neural stem cells) or the effect of a cystatin C protein on a subject with ALS.

In another embodiment of this aspect of the invention, the inventive method comprises administering to the subject a composition comprising a cysteine protease inhibitor and a pharmaceutically acceptable carrier. The inhibitor can be any molecule that decreases or abolishes the activity of a cysteine protease, such as a competitive or non-competitive inhibitor. Cysteine proteases (e.g., cathepsins B, C, H, L, and S; cystatin F, etc.) are a class of enzymes involved in the formation and hydrolysis of the peptide amide bond and are well known in the art. Cysteine proteases play a role in mammalian cellular turnover and apoptosis. The mechanism of action of a cysteine protease involves attack of the nucleophilic thiol of an enzyme's cysteine residue on the carbonyl of the scissile amide bond of a bound substrate. The covalent intermediate that is formed is subsequently hydrolyzed to generate an amine and a carboxylic acid while also regenerating the free enzyme.

In another embodiment of this aspect of the invention, the inventive method comprises administering to the subject a composition comprising a neuroendocrine protein and a pharmaceutically acceptable carrier. A neuroendocrine protein is any protein that is expressed in or secreted by neural or endocrine tissues. The protein can be, for example, neuropeptide Y, somatostatin, galanin, or vasopressin.

In another aspect, the present invention also provides a method for determining the susceptibility of a subject to developing ALS. The method comprises (a) obtaining a sample from the subject, (b) isolating from the sample a transthyretin protein or nucleic acid encoding a transthyretin protein, and (c) determining sequence of transthyretin protein or nucleic acid encoding transthyretin protein obtained from the sample, wherein a varient transthyretin protein or nucleic acid molecule encoding a variant of the transthyretin protein indicates that the subject is susceptible to developing ALS.

The term "sample", as used herein refers to biological material isolated from an animal. The animal can be any suitable animal, but preferably is a mammal, such as a mouse, rat, monkey, or human. It is contemplated that the aforementioned inventive method can be used to diagnose ALS in animal models of the disease, in which case the subject is a non-human animal (e.g., a mouse, rat, monkey, dog, etc.). In a preferred embodiment, the subject is a human. The sample can contain any suitable biological material, but preferably comprises cells obtained from a particular tissue or biological fluid. The sample can be isolated from any suitable tissue or biological fluid. In this respect, the sample can be blood, blood serum, plasma, urine, or spinal cord tissue. In that ALS affects the central nervous system, the sample preferably is isolated from tissue or biological fluid of the central nervous system (CNS) (i.e., brain and spinal cord). In a preferred embodiment of the invention, the sample is isolated from cerebrospinal fluid (CSF). CSF from ALS patients has been used for biochemical assays that have identified changes in the levels of glutamate, glutamine synthetase, transglutaminase activity, γ-aminobutyric acid, and various markers of oxidative injury (see, e.g., Spreux-Varoquaux, 2002; Shaw, 2000; Smith, 1998).

The sample can be obtained in any suitable manner known in the art, such as, for example, by biopsy, blood sampling, urine sampling, lumbar puncture (i.e., spinal tap), ventricular puncture, and cisternal puncture. In a preferred embodiment of the invention, the sample is obtained by lumbar puncture, which also is referred to as a spinal tap or cerebrospinal fluid collection. Lumbar puncture involves insertion of a spinal needle, usually between the 3rd and 4th lumbar vertebrae, into the subarachnoid space where CSF is collected. In instances where there is lumbar deformity or infection which would make lumbar puncture impossible or unreliable, the sample can be collected by ventricular puncture or cisternal puncture. Ventricular puncture typically is performed in human subjects with possible impending brain herniation. Ventricular puncture involves drilling a hole in the skull and inserting a needle directly into the lateral ventricle of the brain to collect CSF. Cisternal puncture involves insertion of a needle below the occipital bone (back of the skull), and can be hazardous due to the proximity of the needle to the brain stem.

A transthyretin protein or nucleic acid in the sample can be separated by any suitable method known in the art. Suitable methods include, for example, centrifugation, ion exchange chromatography, reversed-phase liquid chromatography, and gel electrophoresis (e.g., one-dimensional or two-dimensional gel electrophoresis). Amino acid and nucleic acid sequencing methods are well known in the art and any suitable method can be utilized (e.g., Edman degradation, Sanger method). A variant of the transthyretin protein is any transthyretin protein which has a protein or nucleic acid sequence that differs from the wild type transthyretin protein of the species from which the sample was obtained. The difference between the wild type protein and the protein isolated from the sample can be a difference in one or more nucleotides or amino acids. For example, amino acid 30 of the wild type protein is valine, but amino acid 30 of the protein from the sample is methionine (e.g., Connors, 2003). Such a difference indicates that the subject is susceptible to developing ALS.

In another embodiment, the present invention provides a method for determining progression of ALS in a subject, which method comprises (a) obtaining a sample from the subject, (b) isolating from the sample a transthyretin protein, (c) analyzing the transthyretin protein from the sample by mass spectroscopy, and (d) determining a mass spectral profile for the sample, wherein the presence of a variant of a wild type transthyretin protein in the sample indicates progression of ALS in the subject.

Once the proteins in the sample are separated as described above, the inventive method comprises analyzing the proteins in the sample by mass spectroscopy. In mass spectroscopy, a substance is bombarded with an electron beam having sufficient energy to fragment the molecule. The positive fragments that are produced (cations and radical cations) are accelerated in a vacuum through a magnetic field and are sorted on the basis of mass-to-charge ratio (m/z). Since the bulk of the ions produced in the mass spectrometer carry a unit positive charge, the value m/z typically is equivalent to the molecular weight of the fragment. Any suitable mass spectroscopy method can be used in connection with the inventive method. Examples of suitable mass spectroscopy methods include matrix-assisted laser desorption/ionization mass spectroscopy (MALDI), matrix-assisted laser desorption/ionization-time of flight (MALDI-TOF) mass spectroscopy, plasma desorption/ionization mass spectroscopy (PDI), electrospray ionization mass spectroscopy (ESI), and surface enhanced laser desorption/ionization-time of flight (SELDI-TOF) mass spectroscopy. In time-of-flight (TOF) methods of mass spectroscopy, charged (ionized) molecules are produced in a vacuum and accelerated by an electric field produced by an ion-optic assembly into a free-flight tube or drift time. The velocity to which the molecules may be accelerated is proportional to the square root of the accelerating potential, the square root of the charge of the molecule, and inversely proportional to the square root of the mass of the molecule. The charged molecules travel down the TOF tube to a detector. Mass spectroscopy methods are further described in, for example, International Patent Application Publication No. WO 93/24834, U.S. Pat. No. 5,792,664, U.S. Patent Application Publication No. 2004/0033530 A1, and Hillenkamp et al., *Matrix Assisted UV-Laser Desorption/Ionization: A New Approach to Mass Spectroscopy of Large Biomolecules, Biological Mass Spectroscopy*, Burlingame and McCloskey, eds., Elsevier Science Publ., pp. 49-60 (1990), the disclosures of which are incorporated herein.

In a preferred embodiment of the invention, the proteins in the sample are analyzed by SELDI-TOF mass spectroscopy. Surface enhanced desorption/ionization processes refer to those processes in which the substrate on which the sample is presented to the energy source plays an active role in the desorption/ionization process. In this respect, the substrate (e.g., a probe) is not merely a passive stage for sample presentation. Several types of surface enhanced substrates can be employed in a surface enhanced desorption/ionization process. In one embodiment, the surface comprises an affinity material, such as anion exchange groups or hydrophilic groups (e.g., silicon oxide), which preferentially bind certain classes of molecules. Examples of such affinity materials include, for example, silanol (hydrophilic), $C_8$ or $C_{16}$ alkyl (hydrophobic), immobilized metal chelate (coordinate covalent), anion or cation exchangers (ionic) or antibodies (biospecific). The sample is exposed to a substrate bound adsorbent so as to bind analyte molecules according to the particular basis of attraction. When the analytes are biomolecules (e.g., proteins), an energy absorbing material (e.g., matrix) typically is associated with the bound sample. A laser is then used to desorb and ionize the analytes, which are detected with a detector. For SELDI-TOF mass spectroscopy, the mass accuracy for each protein peak is +/−0.2%. SELDI-TOF mass spectroscopy systems are commercially available from, for example, Ciphergen Biosystems, Inc. (Fremont, Calif.). Surface enhanced desorption/ionization methods are described in, e.g., U.S. Pat. Nos. 5,719,060, 6,294,790, and 6,675,104, and International Patent Application Publication No. WO 98/59360, the disclosures of which are incorporated herein.

One of ordinary skill in the art will appreciate that the output of a mass spectroscopy analysis is a plot of relative intensity as a function of the mass-to-charge ratio (m/z) of the proteins in the sample, which is referred to as a "mass spectral profile" or "mass spectrum." The mass spectral profile, which typically is represented as a histogram depicting protein "peaks," serves to establish the molecular weight and structure of the compound being analyzed. Thus, the inventive method further comprises determining a mass spectral profile for the sample. The most intense peak in the spectrum is termed the base peak, and all other peaks are reported relative to the intensity of the base peak. The peaks themselves are typically very sharp, and are often simply represented as vertical lines.

The ions that are formed by fragmentation of the proteins in the sample during mass spectroscopy are the most stable cations and radical cations formed by the protein molecules. The highest molecular weight peak observed in a spectrum typically represents the parent molecule less an electron, and is termed the molecular ion (M+). Generally, small peaks are also observed above the calculated molecular weight due to the natural isotopic abundance of $^{13}C$, $^{2}H$, etc. Many molecules with especially labile protons do not display molecular ions. For example, the highest molecular weight peak in the mass spectrum of alcohols occurs at an m/z one less than the molecular ion (m−1). Fragments can be identified by their mass-to-charge ratio, but it is often more informative to identify them by the mass which has been lost. For example, loss of a methyl group will generate a peak at m−15, while loss of an ethyl will generate a peak at m−29.

After the mass spectral profile for the sample has been determined, the profile is then compared to that of a wild type transthyretin protein from the same species from which the sample was obtained. A mass shift in the mass spectral profile of the sample, when compared with the wild type mass spectral profile, indicates diagnosis or progression of ALS in the source of the sample.

In another embodiment, the invention provides a method for determining progression of ALS in a subject. The method comprises (a) obtaining a sample from the subject, (b) isolating from the sample a transthyretin protein, (c) analyzing the transthyretin protein levels from the sample, and (d) comparing the protein levels to transthyretin protein levels obtained from the same subject at an earlier time, wherein a change in the protein levels indicates progression of ALS in the subject.

Once the protein has been isolated, the amount of protein in the sample can be determined using any acceptable technique, such as mass spectroscopy and immunological techniques (e.g., immunoblotting, ELISA), which are well known in the art.

The protein levels described above can be compared to any protein levels obtained from the same subject at any point in time which is earlier than the time at which the protein levels were obtained. The determination of the progression of ALS in a subject can be made if a sample obtained from the subject, when compared with a sample obtained from the same animal at an earlier time, comprises either lower or higher levels of transthyretin protein. For example, a sample taken from the CSF of a subject may have higher levels of TTR, whereas a sample taken from spinal cord or brain tissue may have lower levels of TTR.

In another embodiment, the invention provides a method for determining progression of ALS in a subject. The method comprises (a) obtaining a sample from the subject, (b) isolating from the sample a cystatin C protein, (c) analyzing the cystatin C protein levels from the sample, and (d) comparing the protein levels to cystatin C protein levels obtained from the same subject at an earlier time, wherein a change in the protein levels indicates progression of ALS in the subject. The method can be performed substantially as described above. Once the protein has been isolated, the amount of protein in the sample can be determined using any acceptable technique, such as mass spectroscopy and immunological techniques (e.g., immunoblotting, ELISA), which are well known in the art.

The protein levels described above can be compared to any protein levels obtained from the same subject at any point in time which is earlier than the time at which the protein levels were obtained. The determination of the progression of ALS in a subject can be made if a sample obtained from the subject, when compared with a sample obtained from the same animal at an earlier time, comprises either lower or higher levels of cystatin C protein. For example, a sample taken from the CSF of a subject may have higher levels of cystatin C, whereas a sample taken from spinal cord or brain tissue may have lower levels of cystatin C.

EXAMPLES

General Procedures

Subjects

Subjects for the studies described in this application included Caucasian and African American males and females between the ages of 21-85. Samples were obtained from subjects at both the University of Pittsburgh School of Medicine (Pittsburgh, Pa.) and Massachusetts General Hospital (Boston, Mass.). Cerebrospinal fluid (CSF) was obtained by lumbar puncture, immediately centrifuged at 1500 rpm for 5 min at 4° C. to remove cellular debris, aliquoted, frozen at −80° C. and thawed on ice prior to use. 2D-Quant kits (Amersham, USA) were used to determine protein concentrations (0.06 μg/μl to 0.6 μg/μl for each CSF sample). University of Pittsburgh Institutional review board (IRB) and Massachusetts General Hospital IRB approved informed consent for this procedure.

ELISA

ELISA was used to quantify the amount of TTR protein present in the CSF of ALS and control subjects. Dilute human prealbumin in 1×PBS was used to create a standard curve. Samples of 200 uL were diluted 1:2000 in 1×PBS. 50 uL of the standard solutions and sample solutions were dispensed in triplicate to 96 well plate, in addition to 50 uL of wash buffer in triplicate. The wells were allowed to dry overnight on an Eppendorf Thermomixer set to 37 C and 300 rpm. After the wells were completely dried, they were washed at least 3 times with 0.1% Tween-20 in 1×PBS. Washing is done by using a squirt bottle and forcefully filling each well with about 30 uL of the wash solution. Each well is aspirated after washing. The top of the plate was dried by inverting it and blotting against a clean paper towel. The wells were then blocked using SuperBlock blocking buffer in TBS (Pierce) with 0.05% Tween-20 (Sigma Aldrich). 300 uL of the solution was added to each well and then the plate was completely emptied by inversion. This step was repeated 2-3 additional times. The wells were then washed as described at least 3 times. Rabbit anti-human prealbumin (TTR) antibody was diluted to 1:1000 in the wash solution and 50 uL was added to each well. The plate was covered with a disposable plate sealer and incubated at room temperature for 1 hour. The plate sealer was removed and the wells were aspirated and then washed 3 times as described. Goat anti-rabbit Ig-HRP human adsorbed antibody was diluted to 1:5000 in the wash solution. 50 uL was added to each well. The plate was then covered with a disposable plate sealer and incubated at room temperature for 1 hour. The plate sealer was removed and the wells were aspirated and then washed 5 times as described. 50 uL of 3,3',5,5'-Tetramethylbenzidine (TMB) Liquid Substrate System for ELISA was dispended to each well and a blue color was allowed to develop (10-15 minutes). 50 uL of 1M HCl was added to each well to stop color development. The plate was read with a plate reader at 450 nm.

Sample Preparation for Mass Spectroscopy

CSF samples were immunoprecipitated using TTR antibody and mass spectrometric analysis was performed. 50 µL of protein A/G beads were added to each sample, which were then spun briefly to form a pellet. Excess liquid was removed and the beads were washed with 250 µL of PBS. The beads were spun again and the PBS was removed. The wash was then repeated. After the second PBS wash was removed, 400 µL of PBS and 10 µL of the TTR antibody were added. Each sample was then rotated (at a speed of about 28) at 4° C. for 1 hour. The samples were then spun briefly, the supernatant was removed, and 500 µL of 0.5% NP-40 in PBS was added. The samples were then rotated at 4° C. for about 10 min. The samples were spun briefly, the supernatant was removed, and the detergent wash was repeated. 120 µL of the sample was mixed with 400 µL 0.5% NP-40 in PBS and then vortexed briefly. After the supernatant was removed from the beads, the sample/detergent mixture was returned to its corresponding tube, and rotated overnight at 4° C. The samples were spun briefly, and the supernatant was removed. The beads were washed with 500 µL of 0.5% NP-40 in PBS, and the mixture was rotated in the cold room for about 10 min. Each tube was spun, the supernatant was removed, and the detergent wash was repeated. After the supernatant was removed, each sample was washed twice with PBS. The beads were washed with 100 mM Hepes (pH 7.5) to remove salt from the PBS. The bound proteins were eluted with 15 µL of 0.1% TFA in 50% ACN. 10 µL of 100 mmol/L TCEP was added to each sample. The samples were incubated for 20 min. at 55° C.

Mass Spectroscopy

Mass spectroscopy performed in immunoprecipitation experiments or experiments incorporating ion exchange prefractionation of the samples was performed using SELDI ProteinChip® technology (Ciphergen Biosystems, Inc., Fremont, Calif.). A gold chip was washed with water, and then rinsed with a mild detergent (RBS 35). The chip was rinsed again with water, then with methanol, and placed on a heat block at 37° C. to dry. The matrix was prepared by adding approximately 1.0 mL of 0.1-0.5% TFA in 50% ACN to a small amount of sinapic acid. The solution was vortexed and the mixture was spun down to form a pellet. The supernatent was removed and 5 µL of the eluted protein mixture was added to 5 µL of supernatant matrix (1:1 ratio). 2 µL of the protein/matrix mixture was spotted onto its corresponding well of the chip. After drying, an additional 2 µL of sample was added to each well. Once dry, samples were analyzed.

In addition, three separate experimental runs for each ProteinChip were performed. Therefore, each sample was analyzed in duplicate within each experiment, and each experiment was repeated three times. For each experiment, one CSF sample was used as an internal standard to compare peak intensities from four selected m/z peaks to measure variability of the mass spectra. The coefficient of variance (CV) for these selected peaks was less than 25%.

External calibration of the Protein Chip Reader was performed using the Ciphergen All-in-One peptide/protein standard mix containing peptides ranging from 1000 Da to 20 kDa. The dried chips were immediately loaded into the calibrated Chip Reader using optimal laser intensity and detector sensitivity with a mass deflector setting of 1000 Da for low mass range (2-20 kDa) and 10,000 kDa for high mass range (20 kDa-80 kDa). These settings were kept constant for all the chips of every experiment. The mass/charge (m/z) ratios were determined using time of flight (TOF) analysis.

Mass spectroscopy was also performed using strong anion exchange surface (Q10) and IMAC ProteinChips® (Ciphergen Biosystems, Inc., Palo Alto, Calif.). Q10 chips were placed in a bioprocesser (Ciphergen Biosystems, inc., Palo Alto, Calif.) and equilibrated with 200 µL of 100 mM Hepes pH 7.3 (titrated with $NH_4OH$) for ten minutes on a micromix shaker (set at 20/7). Hepes was removed and 100 µL of each sample was applied to the wells. The IMAC Protein Chips were first treated with 100 mM zinc sulfate followed by washing with 50 mM sodium acetate prior to addition of sample. All samples were done in duplicate. A control CSF sample was applied to a different spot of each ProteinChip®. The arrays were then incubated for 30 minutes at room temperature on a micromix (set at 20/7). The CSF was removed and 200 uL of Hepes pH 7.3 (titrated with $NH_4$ OH) was added to each well. The arrays were placed on the micromix for ten minutes (set at 20/7). After ten minutes the Hepes was removed and 200 uL of Hepes was added to the arrays, which were then shaken for another 10 minutes. The ProteinChips® were then removed from the bioprocesser and, using a squirt bottle, rinsed quickly five times with HPLC water pH 7.3 (titrated with $NH_4OH$). Any excess water was blotted off with a Kimwipe® and the ProteinChips® were left to dry. Once dry, the ProteinChips® were placed on a heat block (set at 40° C.) and 1.5 µL of Sinapinic Acid (SPA) (Fluka) in 50% v/v acetonitrile and 0.3% v/v trifluoroacetic acid was added twice to each spot. The Q10 arrays were then read in a Ciphergen PBS IIC Chip reader system containing an autoloader (Ciphergen Biosystems). Spectra were generated using a laser intensity range of 190 and a detector sensitivity range of 8-9 with a mass deflector setting of 1000 Da for the low mass range (1-20 kDa). These settings were kept constant for all chips analyzed in an experiment. Two mass spectra were obtained for each sample: one for the mass range of 1-20 kDa, and a second for the mass range from 20-160 kDa. For each Q10 ProteinChip array, a standard CSF sample was loaded onto one spot to measure chip-to-chip variability. The coefficient of variance (COV) for four-selected m/z signals was less than 30% across all chip arrays. External calibration of the spectrometer was performed using the "7-in-1" peptide mix from Ciphergen Biosystems [(vasopressin (1084.247 Da), somatostatin (1637.903 Da), porcine dynorphin A (2147.5 Da), human ACTH (2933.5 Da), bovine insulin B chain (3495.941 Da), human recombinant insulin (5807.633 Da), and hirudin (7033.614 Da)]. Human SOD1 (15591.4 Da) was also added to this mix.

Protein profile comparisons were made after normalization of each spectrogram to total ion current, and raw spectral data consisted of 37,000 mass peak values for each individual sample. All samples within each sample set were prepared and analyzed at the same time within the same experiment. Spectra were analyzed using Ciphergen ProteinChip software (Version 3.2.1). Statistical analysis of all mass peaks was performed using the nonparametric Mann-Whitney test on the maximal intensity of each peak. Peak labeling was performed using second-pass peak selection with a signal to noise ratio of 1.5. Significance threshold was set of $p<0.05$.

All CSF samples were analyzed by mass spectroscopy for the presence of hemoglobin peaks (15.1 and 15.9 kDa mass peaks). The presence of these distinctive peaks denotes the presence of blood contamination. Such samples were not used and eliminated from further analysis.

Example 1

This example demonstrates different TTR spectral patterns in ALS and control subjects.

FIG. 1 shows results obtained from the Ciphergen Protein chip reader. The CSF from 30 ALS and 15 healthy control or disease control (multiple sclerosis) subjects was analyzed for the presence or absence of TTR mass alterations. TTR was immunoprecipitated using an antibody specific to human transthyretin as described above. Proteins eluted from the anti-TTR coated beads was directly added to gold coated Protein Chips (Ciphergen) and read on the mass spectrometer. A series of 4-5 mass spectral peaks are typically observed for transthyretin. A characteristic TTR pattern is shown for both healthy and disease control subjects (top 4 panels). However, 30% of ALS subjects exhibited split mass spectral peaks for transthyretin (bottom 3 panels). This suggests either altered post-translational modifications to transthyretin or genetic polymorphisms of transthyretin causing altered amino acid composition of the protein occurs in sporadic ALS patients.

Example 2

This example demonstrates mass spectral shifts of TTR in ALS patients using MALDI-TOF-MS.

Figure 2:
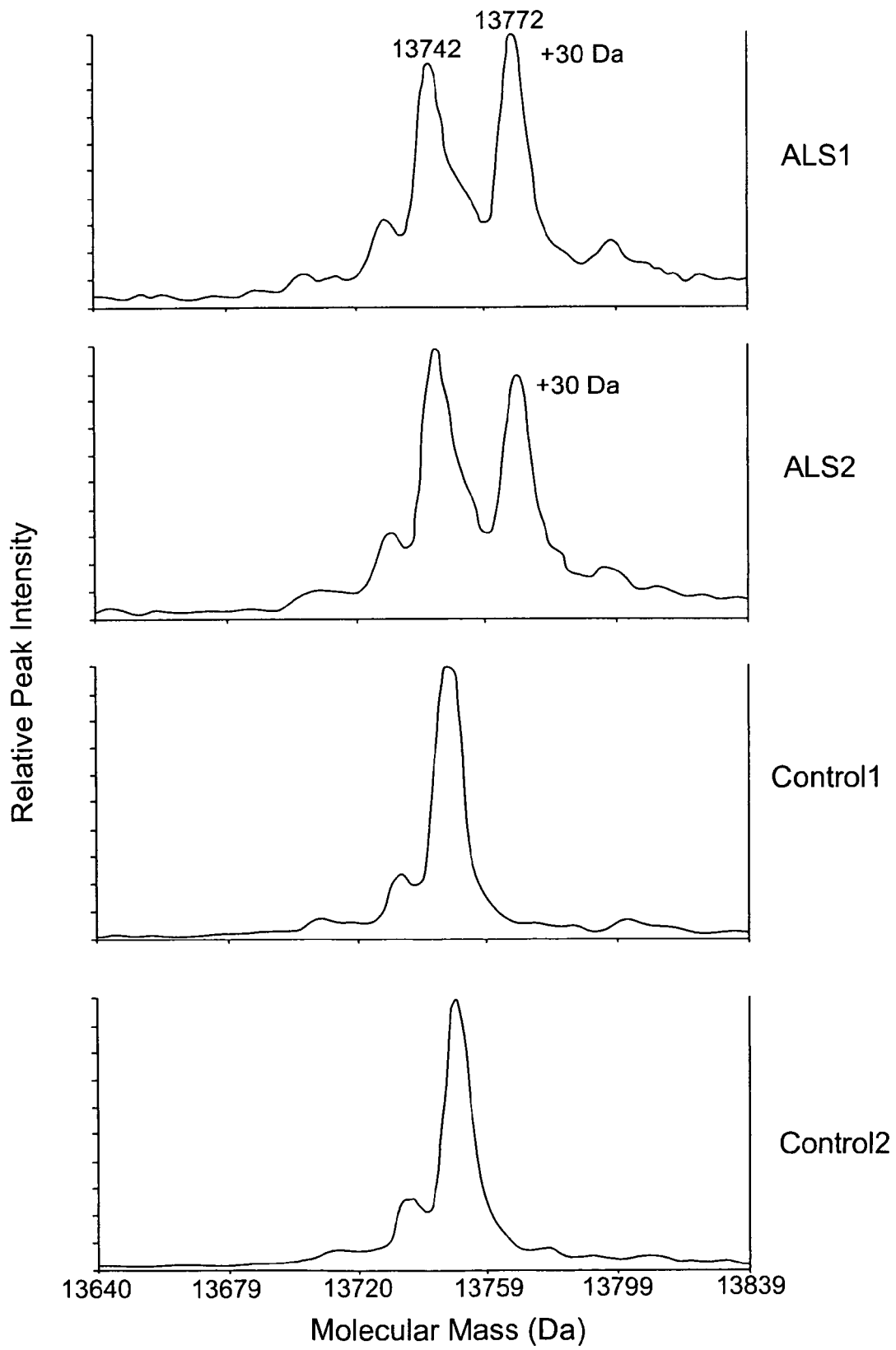
FIG. 2 presents data demonstrating transthyretin mass shifts in ALS patients. Immunoprecipitated transthyretin (TTR) was treated with tris(2-carboxyethyl)phosphine (TCEP) and examined by mass spectrometry using an ABI Voyager/DE mass spectrometer. Control subjects (bottom panels, labeled control 1 and control 2) exhibit a mass peak of 13742 Daltons (Da) and a minor shoulder at approximately 13732 Da. For ALS patients (top panels, labeled ALS1 and ALS2), a TTR doublet with a second peak of approximately 13772 Da (30 Da mass shift) was observed. This additional TTR peak was seen in 9 of 30 ALS patients whereas only 2 of 20 control subjects exhibited a similar TTR protein doublet. This mass shift is consistent with an amino acid substitution resulting from a genetic polymorphism.

TTR was immunoprecipitated from CSF samples from 30 ALS and 20 healthy or disease control subjects. This high resolution mass spectrometer was used to define any mass changes in TTR with higher resolution as compared to the Ciphergen mass spectrometer used in Example 1. To determine if mass spectral shifts may be due to genetic polymorphisms, transthyretin was immunoprecipitated from each CSF sample and then the reduced the transthyretin using tris(2-carboxyethyl)phosphine (TCEP) for 20 min. Reduction of TTR was necessary to resolve the protein mass peaks such that one can identify mass shifts induced by amino acid substitutions caused by genetic polymorphisms. The reduced TTR protein was then analyzed by mass spectrometry using an ABI Voyager/DE instrument. Within the control subjects, transthyretin is seen as a single major protein peak of 13742 Da. A small shoulder was also observed in all samples. A transthyretin doublet was observed in 9 of 30 (30%) sporadic ALS patients (FIG. 2). The second peak was approximately 30 Da increased mass than the native protein. Both transthyretin peaks were observed in these subjects, suggesting that if the additional peak is due to a genetic polymorphism then the ALS patients are heterozygotic for this polymorphism. The increased molecular mass is consistent with the expected mass shift due to a major transthyretin genetic polymorphism present in the general population. The TTR mass shift was observed in 2 of 20 (10%) control subjects. Therefore, a threefold increase was observed in this specific transthyretin mass shift in the ALS population. This result was further confirmed by the immuno-SELDI-TOF-MS TTR data shown in FIG. 3. A specific polymorphism has been identified, which appears to be increased in sporadic ALS patients and may be a risk factor for the disease (Goodall, 2005). This is one example of a genetic polymorphism that may contribute to sporadic ALS. Polymorphisms in the transthyretin gene are proposed to constitute another genetic risk factor for ALS.

Example 3

This example demonstrates increased levels of TTR in the CSF of ALS subjects.

Figure 4:
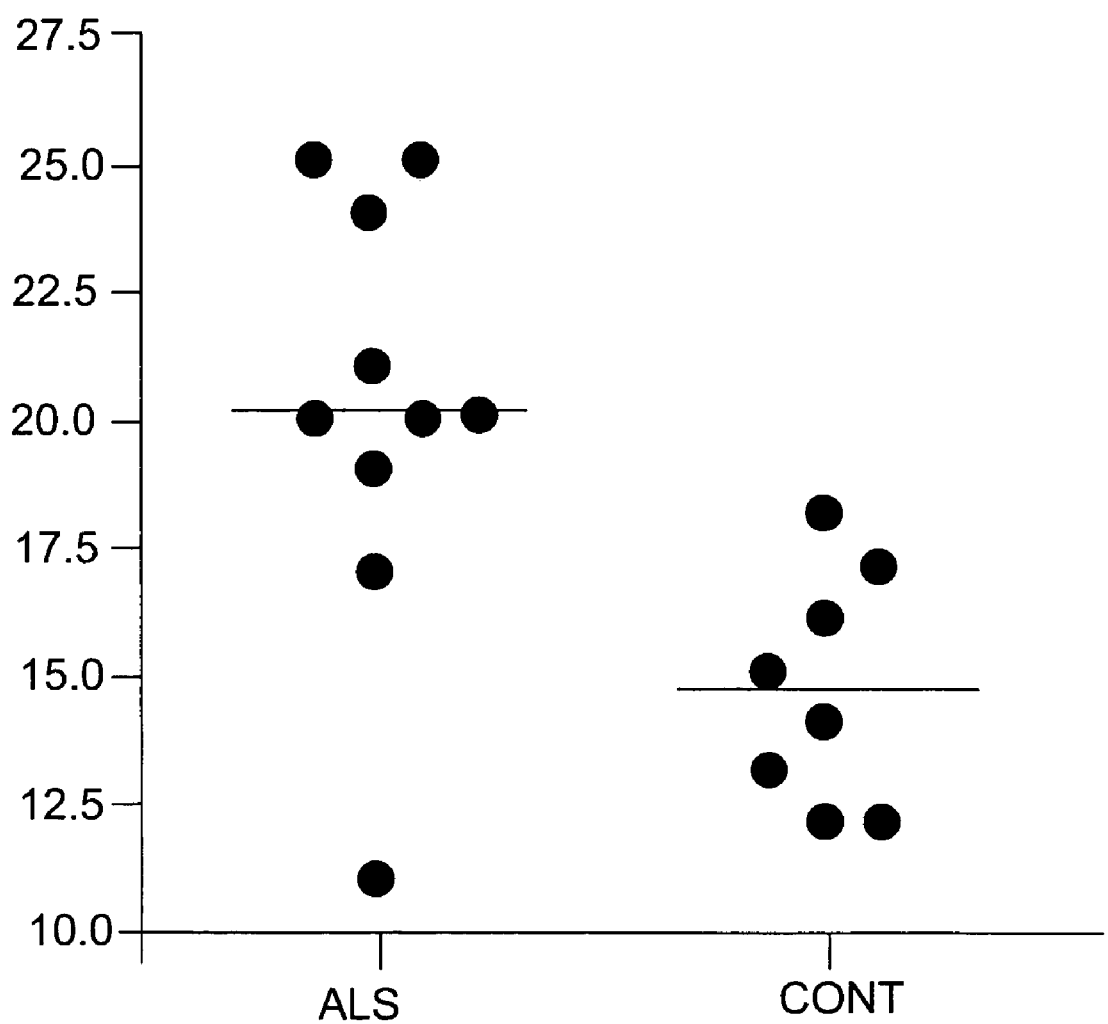
FIG. 4 presents data demonstrating an overall increase in the total level of TTR in the CSF of ALS patients relative to control subjects. TTR ELISA data from 10 ALS and 8 control subjects is shown. The total level of TTR in ALS subjects is significantly increased over that present in control subjects. The bar represents the mean average for all samples within the group.

Levels of transthyretin (TTR) in the CSF of control and ALS subjects were examined using sandwich ELISA. The results demonstrated an overall increase in the total level of TTR in the CSF of ALS patients relative to control subjects (FIG. 4). This is due to that fact that individual mass spectral TTR peaks exhibit alterations that result in decreased overall peak intensity values though the total level of TTR protein within the CSF has increased. This data is also contradictory to TTR western blot data using human spinal cord tissue (data not shown), further suggesting that TTR levels may decrease within the spinal cord and brain tissue while increasing within the CSF.

Example 4

This example demonstrates reduced levels of TTR and cystatin C in ALS subjects.

Figure 5A:
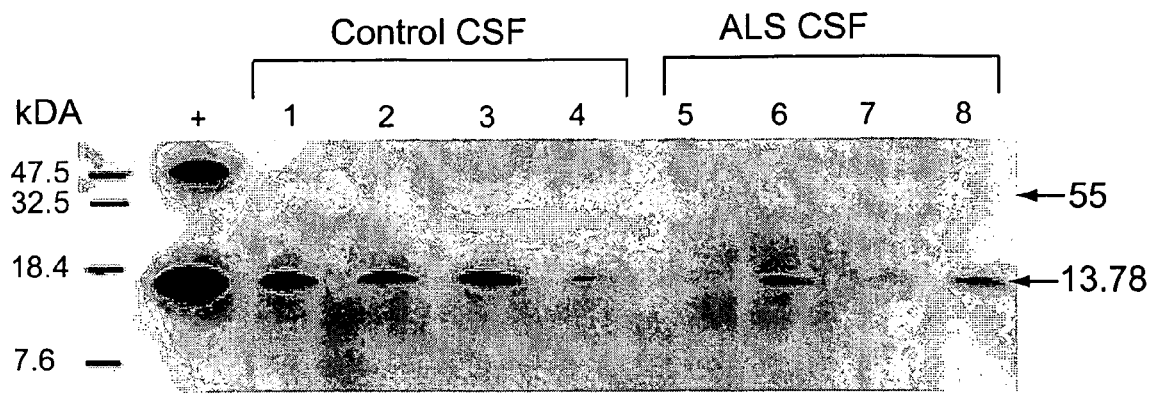
FIG. 5 depicts an immunoblot analysis of TTR and cystatin C. Panel (a) is an immunoblot of TTR protein in control and ALS CSF. 50 82 g of control (lanes 1-4) or ALS (lanes 5-8) CSF were probed for transthyretin (TTR). Purified human TTR (50 ng) was used as a positive control (lane "+"). The arrows on the right indicate the monomeric and homotetrameric forms of TTR protein. Panel (b) is an immunoblot of cystatin C protein in control and ALS CSF. 25 μg of total CSF protein from control (lanes 1-4) or ALS (lanes 5-8) subjects were probed for cystatin C. Purified human cystatin C (10 ng) was used as a positive control (lane "+"). Molecular weight markers indicated in kDa are listed to the left of the positive control lanes in (a) and (b). Panel (c) is a densitometric quantification of TTR and cystatin C proteins from panels (a) and (b) using NIH 1.58 software. The relative abundance was expressed per amount of CSF protein loaded per gel lane and the height of the bars corresponds to the average value for each protein in control and ALS subjects +/− standard error mean (SEM). Single factor ANOVA was performed with a confidence interval of 95% to compare the protein levels of controls and ALS. The p values for TTR and cystatin C were 0.03 and 0.04, respectively. Asterisks indicate the statistical significance.
Figure 5B:
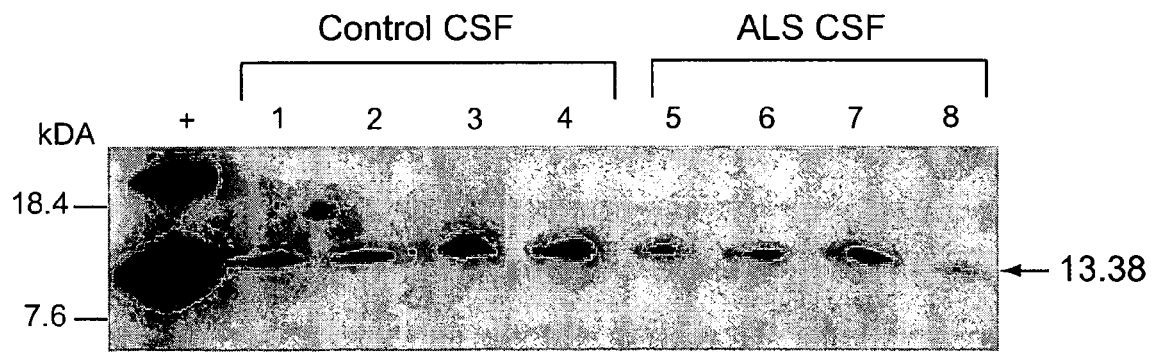
Figure 5C:
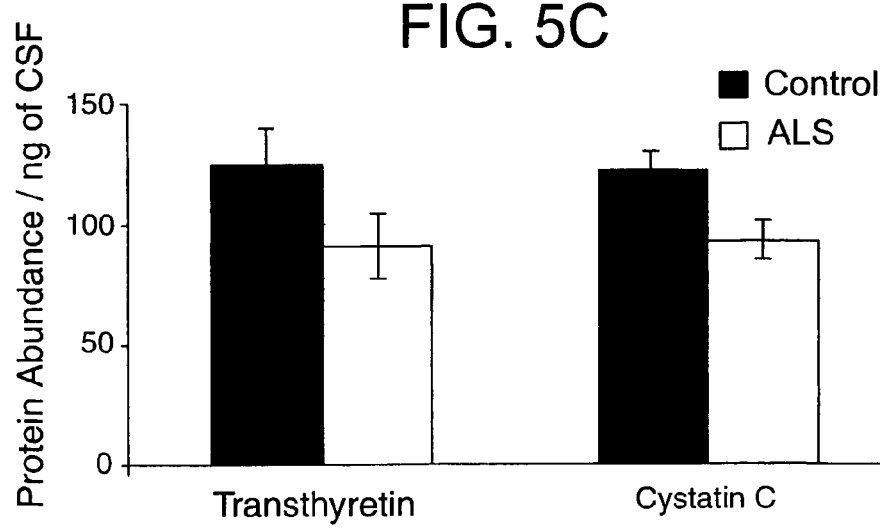

Immunoblotting for cystatin C and transthyretin was performed using a separate cohort of recently diagnosed ALS and control subjects (FIG. 5). 25 or 50 µg of CSF protein from controls (n=17) and ALS (n=17) subjects were electrophoresced on a 10-20% Tris-Tricine Ready Gels (BioRad Laboratories, USA) and transferred to a PVDF membrane. The control group included 6 healthy subjects, 2 multiple sclerosis, 2 lyme disease, 2 normal pressure hydrocephalus, 1 dementia, 1 epilepsy, 1 myopathy, 1 meningitis, and 1 neurofibromatosis subjects. The primary antibodies were used at a dilution of 1:500. For protein confirmation we loaded 10 ng of purified human cystatin C protein (Calbiochem, USA) or 50 ng of transthyretin (Biodesign, USA) into separate gel lanes. These results demonstrate that the level of the 13.8 kDa TTR monomer is significantly reduced in the CSF of ALS subjects as compared to control CSF. The immunoblot also revealed the presence of a 55 kDa peak that represents the homotetramer form of TTR. The level of homotetramer was also increased in control subjects. In addition, the level of cystatin C was reduced in the CSF of ALS subjects as compared to CSF from control subjects. Although not wishing to be bound by any particular theory, it is likely that the ELISA analysis (Example 3) identified a more complete set of TTR proteins due to the use of multiple, less specific antibodies, thus resulting in an increase in the total level of TTR in the CSF of ALS patients. The antibody utilized in the immunoblot, however, was specific to the TTR biomarker, the levels of which decrease in the CSF of ALS patients. Therefore, although total TTR levels increase in the CSF of ALS patients, the TTR biomarker levels decrease.

Example 5

This example demonstrates decreased levels of TTR in the motor neurons of ALS subjects.

Figure 6:
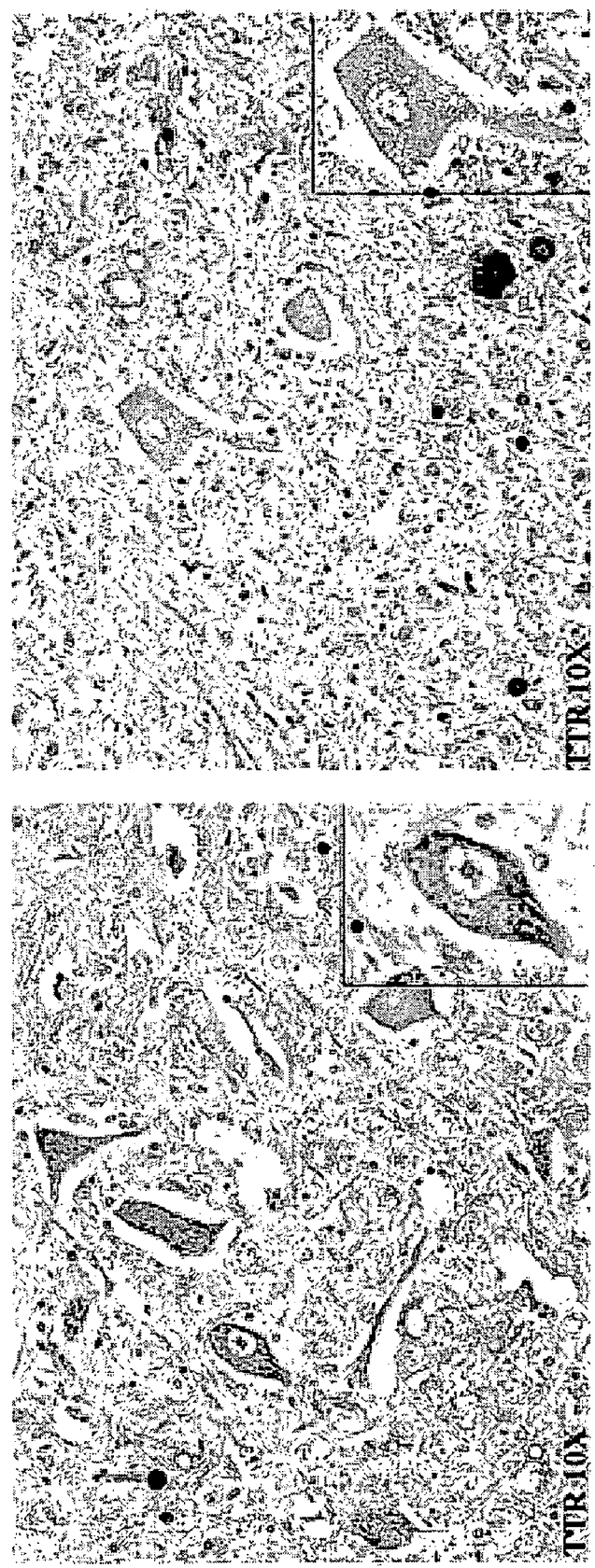
FIG. 6 depicts an immunohistochemical analysis of a cross section of lumbar spinal cord tissue. Lumbar spinal cord tissue sections from 7 control and 7 ALS subjects were used to determine TTR immunoreactivity in motor neurons using anti-TTR antibody. In control subjects, TTR was present within the cytoplasm of motor neurons, often in a speckled pattern (left panel). In ALS spinal cord we observed decreased levels of TTR in surviving motor neurons (right panel). Both panels are at 10× magnification. Insets in both panels are high magnification image (40×) of a motor neuron. Therefore decreased levels of TTR are present in surviving motor neurons in ALS subjects.

Immunohistochemistry for transthyretin by light microscopy was performed with paraffin embedded lumbar spinal cord sections from archived post-mortem tissues from the University of Pittsburgh ALS Tissue Bank. Neuropathologic assessment confirmed the clinical diagnosis of ALS or the lack of any central nervous system abnormalities within the control subjects. Healthy controls (n=8) and ALS (n=16) cases were probed with anti-rabbit polyclonal antibodies (DAKO, Denmark) at a concentration of 1:300. All sections were immunostained simultaneously and examined in a coded manner by two independent investigators. Controls included tissue sections lacking either primary or secondary antibody. The results demonstrate decreased levels of TTR in surviving motor neurons in ALS subjects (FIG. 6). Thus, TTR levels are decreased in the motor neurons of ALS subjects.

Example 6

This example demonstrates alterations in transthyretin (FIG. 8) and cystatin C (FIG. 7) protein levels (13.4 kDa peak) in 3 ALS subjects over a 12-month timeframe.

In FIG. 7, patient 1 exhibits a linear decrease in cystatin C levels over a 12-month time frame. Patient 2 fails to exhibit cystatin C alterations, indicating that not every ALS patient can be followed for disease progression by this single marker. Patient 3 also exhibits continued decreased levels of the full-length cystatin C protein peak over a 12-month period. Samples were analyzed using Q10 Protein Chips and the Ciphergen mass spectrometer.

Figure 8:
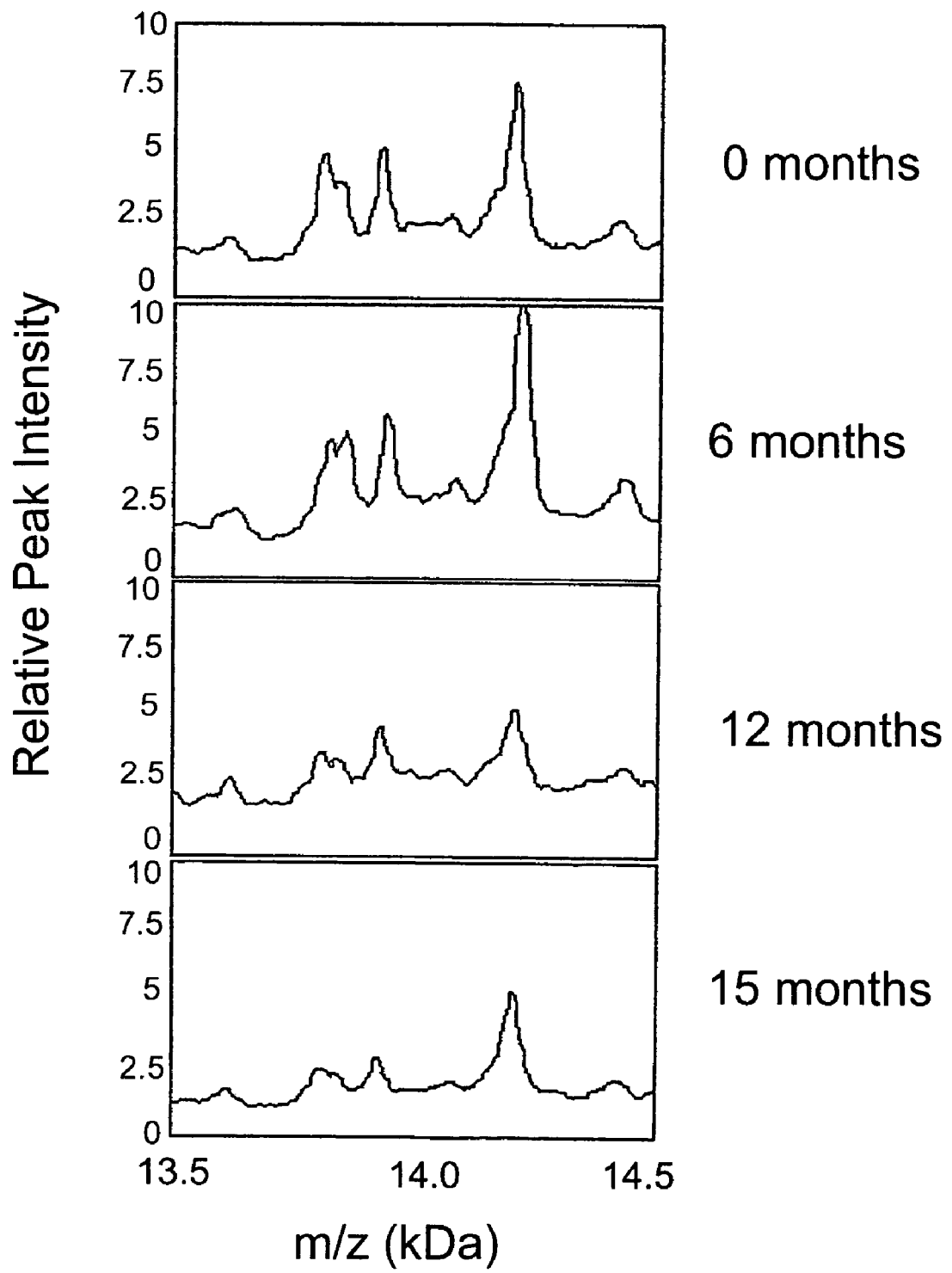
FIG. 8 presents data demonstrating alterations in transthyretin protein mass spectral peaks within an ALS patient over time. The data was obtained using a zinc coated Ciphergen IMAC-30 Protein Chip and analyzed on the Ciphergen mass spectrometer.

FIG. 8 shows the fluctuation in TTR levels in a patient over a 15 month time frame. The TTR peaks reside between 13.8-14.3 kDa region of these spectra. At Time 0 months the patient has already been diagnosed with ALS and therefore this TTR signature is already abnormal when compared to a healthy control subject. At 6 months there are additional alterations to the first mass peak doublet at approximately 13.8 kDa. At both 12 and 15 months there are additional decreases in TTR peak intensity values that correlate with clinical measures of disease progression.

All references, including publications, patent applications, and patents, cited herein, including the following bibliography, are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein is intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Abrahamson et al., "Structure and expression of the human cystatin C gene.", Biochem J. 1;268(2), 287-94 (1990).

Bensonet al., "Identification of carriers of a variant plasma prealbumin (transthyretin) associated with familial amyloidotic polyneuropathy type I", J Clin Invest 75, 71-75 (1985).

Bergen et al., "Identification of transthyretin variants by sequential proteomic and genomic analysis", Clin Chem., 50:1544-1552 (2004).

Bernstein et al., "Transthyretin: Its response to malnutrition and stress injury. Clinical usefulness and economic implications", Clin Chem Lab Med 40, 1344-1348 (2002).

Borchelt et al., "Superoxide dismutase 1 with mutations linked to familial amyotrophic lateral sclerosis possesses significant activity", Proc. Natl. Acad. Sci. USA, 91, 8292-8296 (1994).

Chaudhuri et al., "The neuroendocrine protein 7B2 acts as a molecular chaperone in the in vitro folding of human insulin-like growth factor-1 secreted from yeast", Biochem Biophys Res Comm., 211:417-425 (1995).

Cleveland et al., "From Charcot to Lou Gehrig: deciphering selective motor neuron death in ALS", Nat. Rev. Neurosci., 2, 806-19 (2001).

Connors et al., "Tabulation of human transthyretin (TTR) variants", Amyloid, 10, 160-184 (2003).

Corcoran et al., "Absence of retinoids can induce motoneuron disease in the adult rat and a retinoid defect is present in motoneuron disease patients", J Cell Sci 115, 4735-4741 (2002).

Desnuelle et al., Amyotrophic Lateral Sclerosis & Other Motor Neuron Disorders, 2, 9-18 (2001).

Fernandez et al., "Thyroid hormone administration enhances remyelination in chronic demyelinating inflammatory disease", Proc. Natl. Acad. Sci. USA, 101:16363-16368 (2004).

Goodall, et al., "Association of the H63D polymorphism in the hemochromatosis gene with sporadic ALS", Neurology, 65, 934-937 (2005).

Groeneveld et al., "A randomized sequential trial of creatine in amyotrophic lateral sclerosis", Annals of Neurology, 53, 437-45 (2003).

Kamel et al., "Lead exposure and amyotrophic lateral sclerosis", *Epidemiology* 13, 311-319 (2002).

Kim et al., "PARP expression is increased in astrocytes but decreased in motor neurons in the spinal cord of sporadic ALS patients", *J. Neuropathol. Exp. Neurol.*, 62, 88-103 (2003).

Martens et al., "The novel pituitary polypeptide 7B2 is a highly-conserved protein coexpressed with proopiomelanocortin", *Eur. J. Biochem.*, 181, 75-70 (1989).

Mbikay et al., "Neuroendocrine secretory protein 7B2: structure, expression and functions", *Biochem J.*, 357:329-342 (2001).

Menzies et al., "Mitochondrial dysfunction in a cell culture model of familial amyotrophic lateral sclerosis", *Brain*, 125, 1522-1533 (2002).

Mey et al., "Retinoic acid signaling in the nervous system of adult vertebrates", *Neuroscientist* 10, 409-421 (2004).

Miller et al., *Amyotrophic Lateral Sclerosis & Other Motor Neuron Disorders*, 4, 191-206 (2003).

Nagai et al., "Rats expressing human cytosolic copper-zinc superoxide dismutase transgenes with amyotrophic lateral sclerosis: associated mutations develop motor neuron disease", *J. Neurosci.*, 21, 9246-9254 (2001).

Palha, "Transthyretin as a thyroid hormone carrier: Function revisited", *Clin Chem Lab Med* 40, 1292-1300 (2002).

Paquet et al., "The neuroendocrine precursor 7B2 is a sulfated protein proteolytically processed by a ubiquitous furin-like convertase", *J Biol Chem.*, 29;269(30):19279-85 (1994).

Ranganathan et al., "Alterations in G(1) to S phase cell-cycle regulators during amyotrophic lateral sclerosis", *Am. J. Pathol.*, 162, 823-835 (2003).

Ranganathan et al., "Proteomic profiling of cerebrospinal fluid identifies biomarkers for amyotrophic lateral sclerosis", *J Neurochem*, 9, 1461-1471 (2005).

Rosen et al., "Mutations in Cu/Zn superoxide dismutase gene are associated with familial amyotrophic lateral sclerosis", *Nature*, 362, 59-62 (1993).

Rosen et al., "A frequent ala 4 to val superoxide dismutase-1 mutation is associated with a rapidly progressive familial amyotrophic lateral sclerosis", *Hum Mol Genet*, 3, 981-987 (1994).

Shaw et al., *Amyotrophic Lateral Sclerosis & Other Motor Neuron Disorders*, 1, Suppl. 2, S61-67 (2000).

Smith et al., "Presence of 4-hydroxynonenal in cerebrospinal fluid of patients with sporadic amyotrophic lateral sclerosis", *Ann. Neurol.*, 44, 696-699 (1998).

Sousa et al., "Neurodegeneration in familial amyloid polyneuropathy: from pathology to molecular signaling", *Progr Neurobiol* 71, 385-400 (2003).

Sousa et al., "Deposition of transthyretin in early stages of familial amyloidotic polyneuropathy: evidence for toxicity of nonfibrillar aggregates", *Am J Pathol* 159, 1993-2000 (2001).

Sousa et al., "Evidence for early cytotoxic aggregates in transgenic mice for human transthyretin Leu55Pro", *Am J Pathol* 161, 1935-1948 (2002).

Spreux-Varoquaux et al., "Glutamate levels in cerebrospinal fluid in amyotrophic lateral sclerosis: a reappraisal using a new HPLC method with coulometric detection in a large cohort of patients", *Journal of the Neurological Sciences*, 193, 73-78 (2002).

Stein et al., "Neutralization of transthyretin reverses the neuroprotective effects of secreted amyloid precursor protein (APP) in APPsw mice resulting in tau phosphorylation and loss of hippocampal neurons: Support for the amyloid hypothesis", *J Neurosci* 24, 7707-7717 (2004).

Subramaniam et al., "Mutant SOD1 causes motor neuron disease independent of copper chaperone-mediated copper loading", *Nat. Neurosci.*, 5, 301-307 (2002).

Tsuzuki et al., "Transthyretin binds amyloid beta peptides, Abeta1-42 and Abeta1-40 to form complex in the autopsied human kidney-possible role of transthyretin for Abeta sequestration", *Neurosci Lett* 281, 171-174 (2000).

Vinceti et al., "Lead, cadmium, and selenium in the blood of patients with sporadic amyotrophic lateral sclerosis", *Ital J Neurol Sci* 18, 87-92 (1997).

Zheng et al., "Transthyretin, thyroxine, and retinol-binding protein in human cerebrospinal fluid: effect of lead exposure", *Toxicol Sci* 61, 107-114 (2001).

Zheng, "Toxicology of choroid plexus: Special reference to metal-induced neurotoxicities", *Microscopy Res & Tech* 52, 89-103 (2001).

Zhu et al., "Internal cleavage of the inhibitory 7B2 carboxyl-terminal peptide by PC2: a potential mechanism for its inactivation", *Proc Natl Acad Sci*, 14;93(10):4919-24 (1996).

The invention claimed is:

1. A method comprising
   (a) obtaining a fluid sample selected from the group consisting of cerebrospinal fluid, blood serum, plasma, and urine from an individual at risk of or who has been diagnosed with amyotrophic lateral sclerosis (ALS), (b) analyzing the cystatin C protein levels from the sample, and (c) comparing the cystatin C protein levels to a control sample wherein cystatin C protein levels of the sample that are lower than cystatin C protein levels of the control sample is indicative of ALS.

2. The method of claim 1, wherein the level of cystatin C protein is indicative of the progression of ALS.

3. The method of claim 1, wherein the samples are analyzed by mass spectroscopy.

4. The method of claim 1, wherein the samples are analyzed using immunological techniques.

5. The method of claim 1, wherein the samples are analyzed by ELISA.

6. The method of claim 1, wherein the samples are analyzed by immunoblot.

7. The method of claim 1, wherein the individual is a human.

8. The method of claim 1 wherein the level of protein is compared to a normal control from an individual without ALS.

9. The method of claim 1 wherein the level of protein is compared to a control from an individual with ALS.

10. The method of claim 1 wherein the level of protein is correlated with the progression of ALS in an individual previously diagnosed with ALS.

11. The method of claim 10 wherein the individual is being treated to alleviate one or more symptoms of ALS.

* * * * *

UNITED STATES PATENT AND TRADEMARK OFFICE
CERTIFICATE OF CORRECTION

| | | |
|---|---|---|
| PATENT NO. | : 7,572,596 B2 | Page 1 of 1 |
| APPLICATION NO. | : 11/294161 | |
| DATED | : August 11, 2009 | |
| INVENTOR(S) | : Robert P. Bowser | |

It is certified that error appears in the above-identified patent and that said Letters Patent is hereby corrected as shown below:

Title Page, item (54), and column 1, line 2, title, replace "Neuroendotcrine" with --Neuroendocrine--.

Column 1, lines 14-17, replace "This invention was made in part with Government support under Grant Number ES013469 awarded by the National Institute of Environmental Health Sciences. The Government may have certain rights in this invention." with --This invention was made with government support under Grant Number ES013469, awarded by the National Institutes of Health. The government has certain rights in the invention.--.

Signed and Sealed this
First Day of January, 2013

David J. Kappos
*Director of the United States Patent and Trademark Office*